(12) United States Patent
Gerrans et al.

(10) Patent No.: US 10,898,693 B2
(45) Date of Patent: *Jan. 26, 2021

(54) NASAL DELIVERY OF AGENTS WITH NESTED BALLOON CATHETER

(71) Applicant: Sanovas Intellectual Property, LLC, Reno, NV (US)

(72) Inventors: Lawrence J. Gerrans, San Anselmo, CA (US); Erhan H. Gunday, Great Neck, NY (US)

(73) Assignee: Sanovas Intellectual Property, LLC, Reno, NV (US)

(*) Notice: Subject to any disclaimer, the term of this patent is extended or adjusted under 35 U.S.C. 154(b) by 1097 days.

This patent is subject to a terminal disclaimer.

(21) Appl. No.: 14/748,810

(22) Filed: Jun. 24, 2015

(65) Prior Publication Data

US 2015/0290438 A1 Oct. 15, 2015

Related U.S. Application Data

(63) Continuation-in-part of application No. 13/715,654, filed on Dec. 14, 2012, now Pat. No. 9,186,485, (Continued)

(51) Int. Cl.
*A61M 25/10* (2013.01)
*A61M 5/00* (2006.01)
(Continued)

(52) U.S. Cl.
CPC ........... *A61M 25/1011* (2013.01); *A61B 1/04* (2013.01); *A61B 5/6853* (2013.01); (Continued)

(58) Field of Classification Search
CPC ............ A61M 25/1011; A61M 25/104; A61M 25/10184; A61M 25/10187; (Continued)

(56) References Cited

U.S. PATENT DOCUMENTS

| 4,186,745 A | 2/1980 | Lewis et al. |
| 4,446,867 A | 5/1984 | Leveen et al. |

(Continued)

FOREIGN PATENT DOCUMENTS

| EP | 1230944 A2 | 8/2002 |
| EP | 1913882 A1 | 4/2008 |

(Continued)

OTHER PUBLICATIONS

International Search Report and Written Opinion of the International Searching Authority; PCT/US2010/034689; dated Jul. 15, 2010; 10 pages.

*Primary Examiner* — Kevin C Sirmons
*Assistant Examiner* — Alexandra Lalonde
(74) *Attorney, Agent, or Firm* — Forge IP, PLLC

(57) ABSTRACT

A method of localized delivery of a therapeutic and/or diagnostic agent to nasal tissue or cavities includes inserting a catheter into a nasal cavity, the catheter having an outer balloon with at least one opening therethrough and an inner surface, and an inner balloon disposed in the outer balloon and at least partially enclosing an inflation chamber and having an outer surface defining a space between the outer surface of the inner balloon and the inner surface of the outer balloon, supplying the agent to the space between the outer surface of the inner balloon and the inner surface of the outer balloon via a first lumen of the catheter, and inflating the inner balloon by supplying fluid to the inflation chamber via a second lumen of the catheter to urge the agent out of the opening in the wall of the outer balloon and into nasal tissue.

23 Claims, 13 Drawing Sheets

Related U.S. Application Data which is a continuation of application No. 13/037,856, filed on Mar. 1, 2011, now Pat. No. 8,348,890.

(51) Int. Cl.
| | | |
|---|---|---|
| *A61B 1/04* | (2006.01) | |
| *A61B 17/32* | (2006.01) | |
| *A61M 29/02* | (2006.01) | |
| *A61B 17/12* | (2006.01) | |
| *A61B 5/00* | (2006.01) | |
| *A61B 5/021* | (2006.01) | |
| *A61N 5/06* | (2006.01) | |
| *A61N 5/04* | (2006.01) | |

(52) U.S. Cl.
CPC ........ *A61B 5/6867* (2013.01); *A61B 17/1204* (2013.01); *A61B 17/12136* (2013.01); *A61B 17/32* (2013.01); *A61M 5/007* (2013.01); *A61M 29/02* (2013.01); *A61B 5/021* (2013.01); *A61B 5/4839* (2013.01); *A61B 2017/12004* (2013.01); *A61B 2017/320004* (2013.01); *A61M 25/10184* (2013.11); *A61M 2025/105* (2013.01); *A61M 2025/1013* (2013.01); *A61M 2025/1022* (2013.01); *A61M 2025/1052* (2013.01); *A61M 2025/1086* (2013.01); *A61M 2202/048* (2013.01); *A61M 2202/0468* (2013.01); *A61M 2205/3303* (2013.01); *A61M 2210/0618* (2013.01); *A61N 5/045* (2013.01); *A61N 5/062* (2013.01); *A61N 5/0603* (2013.01); *A61N 2005/0607* (2013.01)

(58) Field of Classification Search
CPC .... A61M 25/10188; A61M 2025/1013; A61M 2025/1086; A61M 2025/1088; A61M 2025/105; A61M 2025/1084
See application file for complete search history.

(56) References Cited

U.S. PATENT DOCUMENTS

| | | | |
|---|---|---|---|
| 4,773,899 A | 9/1988 | Spears | |
| 4,824,436 A | 4/1989 | Wolinsky | |
| 4,921,484 A | 5/1990 | Hillstead | |
| 4,994,033 A | 2/1991 | Shockey et al. | |
| 5,049,132 A | 9/1991 | Shaffer et al. | |
| 5,100,425 A | 3/1992 | Fischell et al. | |
| 5,196,017 A | 3/1993 | Silva et al. | |
| 5,304,121 A | 4/1994 | Sahatjian et al. | |
| 5,304,220 A | 4/1994 | Maginot | |
| 5,336,234 A * | 8/1994 | Vigil ............. | A61B 17/320725 604/103.08 |
| 5,397,307 A | 3/1995 | Goodin | |
| 5,545,133 A | 8/1996 | Burns et al. | |
| 5,611,775 A | 4/1997 | Machold et al. | |
| 5,647,847 A | 7/1997 | Lafontaine et al. | |
| 5,674,192 A | 10/1997 | Sahatjian et al. | |
| 5,707,352 A | 1/1998 | Sekins et al. | |
| 5,728,064 A | 3/1998 | Burns et al. | |
| 5,785,685 A | 7/1998 | Kugler et al. | |
| 5,833,644 A | 11/1998 | Zadno-Azizi et al. | |
| 5,873,852 A | 2/1999 | Vigil et al. | |
| 6,024,693 A | 2/2000 | Schock et al. | |
| 6,048,332 A | 4/2000 | Duffy et al. | |
| 6,129,705 A | 10/2000 | Grantz | |
| 6,190,354 B1 | 2/2001 | Sell et al. | |
| 6,245,008 B1 | 6/2001 | Leschinsky et al. | |
| 6,248,092 B1 | 6/2001 | Miraki et al. | |
| 6,440,158 B1 | 8/2002 | Saab | |
| 6,485,500 B1 | 11/2002 | Kokish et al. | |
| 6,544,221 B1 | 4/2003 | Kokish et al. | |
| 6,616,597 B2 | 9/2003 | Schock et al. | |
| 6,623,452 B2 | 9/2003 | Chien et al. | |
| 6,685,648 B2 | 2/2004 | Flaherty et al. | |
| 6,733,459 B1 | 5/2004 | Atsumi | |
| 7,014,652 B2 | 3/2006 | Cioanta et al. | |
| 7,025,718 B2 | 4/2006 | Williams | |
| 7,462,165 B2 | 12/2008 | Ding et al. | |
| 7,470,252 B2 | 12/2008 | Mickley et al. | |
| 7,569,032 B2 | 8/2009 | Naimark et al. | |
| 7,611,484 B2 | 11/2009 | Wellman et al. | |
| 7,658,966 B2 | 2/2010 | Kokish | |
| 7,727,226 B2 | 7/2010 | Chang et al. | |
| 7,935,044 B2 | 5/2011 | Lubock | |
| 8,182,446 B2 | 5/2012 | Schaeffer et al. | |
| 8,348,890 B2 | 1/2013 | Gerrans et al. | |
| 9,186,485 B2 * | 11/2015 | Gerrans ............. | A61M 25/1011 |
| 2003/0065303 A1 | 4/2003 | Wellman et al. | |
| 2003/0114791 A1 | 6/2003 | Rosenthal et al. | |
| 2004/0044308 A1 | 3/2004 | Naimark et al. | |
| 2004/0064093 A1 | 4/2004 | Hektner et al. | |
| 2005/0015047 A1 * | 1/2005 | Shah ............. | A61M 25/1011 604/101.02 |
| 2005/0015049 A1 | 1/2005 | Rioux et al. | |
| 2005/0107741 A1 * | 5/2005 | Willard ............. | A61F 7/12 604/113 |
| 2006/0004323 A1 * | 1/2006 | Chang ............. | A61B 17/24 604/28 |
| 2006/0200074 A1 * | 9/2006 | Zadno-Azizi .... | A61B 17/12045 604/96.01 |
| 2007/0060942 A2 | 3/2007 | Zadno-Azizi | |
| 2007/0198047 A1 * | 8/2007 | Schon ............. | A61B 17/320725 606/192 |
| 2008/0039791 A1 | 2/2008 | Abboud et al. | |
| 2008/0051627 A1 | 2/2008 | Raju | |
| 2008/0171985 A1 | 7/2008 | Karakoca | |
| 2008/0208118 A1 | 8/2008 | Goldman | |
| 2009/0054922 A1 * | 2/2009 | Broker ............. | A61M 25/1002 606/194 |
| 2009/0105687 A1 | 4/2009 | Deckman et al. | |
| 2009/0171268 A1 | 7/2009 | Williams, Jr. et al. | |
| 2009/0187098 A1 * | 7/2009 | Makower ............. | A61B 1/0661 600/424 |
| 2009/0229374 A1 | 9/2009 | Carlisle et al. | |
| 2009/0240199 A1 * | 9/2009 | Rahimsobhani ...... | A61M 16/04 604/101.02 |
| 2009/0254064 A1 * | 10/2009 | Boatman ............. | A61M 25/1011 604/509 |
| 2010/0069900 A1 | 3/2010 | Shirley et al. | |
| 2010/0113939 A1 | 5/2010 | Mashimo et al. | |
| 2010/0121270 A1 | 5/2010 | Gunday et al. | |
| 2011/0082483 A1 * | 4/2011 | Diamant ............. | A61B 17/320725 606/159 |
| 2011/0152683 A1 | 6/2011 | Gerrans et al. | |
| 2011/0166516 A1 | 7/2011 | Orr | |
| 2011/0218494 A1 | 9/2011 | Gerrans et al. | |
| 2011/0218517 A1 * | 9/2011 | Ogle ............. | A61K 9/006 604/508 |
| 2011/0264039 A1 * | 10/2011 | Thielen ............. | A61M 25/104 604/103.01 |
| 2012/0095292 A1 | 4/2012 | Gunday et al. | |
| 2012/0226103 A1 | 9/2012 | Gunday et al. | |

FOREIGN PATENT DOCUMENTS

| | | |
|---|---|---|
| WO | 9304727 A1 | 3/1993 |
| WO | 2009046206 A1 | 4/2009 |
| WO | 2009086269 A2 | 7/2009 |
| WO | 2010024871 A1 | 3/2010 |

\* cited by examiner

NASAL DELIVERY OF AGENTS WITH NESTED BALLOON CATHETER

FIELD OF THE INVENTION

The present invention relates to methods and systems for delivering therapeutic and/or diagnostic agents to specific cellular locations within and adjacent to bodily tissues and cavities. More specifically, the invention relates to a method and system of localized delivery of diagnostic and/or therapeutic agents to nasal cavities and tissues via a nested balloon catheter.

BACKGROUND OF THE INVENTION

A sinus infection, or sinusitis, is a common condition that affects around 31 million people in the United States each year. The infection occurs when the sinuses and nasal passages become inflamed.

The sinuses are small air pockets located behind a person's forehead, nose, cheekbones, and eyes. The sinuses produce mucus, which is a jelly-like liquid that protects the body by trapping germs. Sometimes bacteria or allergens can cause too much mucus to form, which blocks the openings of the sinuses.

Excess mucus is common when a person has a cold or allergies. This mucus buildup can encourage bacteria and germs to grow in the sinus cavity, leading to a bacterial or viral infection. Most sinus infections are viral, and go away in a week or two without treatment. However, in more severe cases, interventional treatment, including sinus surgery, is necessary, especially in cases of chronic sinusitis.

Functional endoscopic sinus surgery is currently the most common type of surgery used to treat chronic sinusitis. In a typical sinus surgery procedure, an endoscope is inserted into the nostril along with one or more surgical instruments. The surgical instruments are then used to cut tissue and/or bone, cauterize, suction, etc. In most sinus surgery procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. Sinus surgery procedures can be effective in the treatment of sinusitis and for the removal of tumors, polyps and other aberrant growths from the nose.

Another type of the sinus surgery procedures—balloon sinuplasty—is often performed as an outpatient's procedure in doctors' offices under a local anesthesia. During the procedure, the physician inserts a guide catheter through the nostril and near the sinus opening under endoscopic visualization. A flexible guide wire is then introduced into the targeted sinus to confirm access. Once access to a blocked sinus is confirmed, a balloon catheter is advanced over the guide wire and positioned in the blocked sinus opening for inflation, and the balloon is inflated to dilate the sinus.

Because this procedure is performed under local anesthesia, the patient is awake during the procedure. Thus, the insertion of the guide catheter and other instruments through the nostril and into the nasal cavities often causes patient discomfort and anxiety. Additionally, the procedures often cause significant bleeding, requiring nasal packing to be placed in the patient's nose during and after the surgery, which can be uncomfortable for the patient and interfere with normal breathing, eating, drinking, etc. Furthermore, the delivery of local anesthetic requires insertion of a separate drug delivery device before the area is numbed, which causes further patient discomfort and anxiety.

Despite the emerging sinus surgery procedures, there remains a need for further development of new and improved devices and methods for surgical treatment of sinusitis and other ear, nose and throat disorders. In particular, there is a need for an integrated sinus surgery device that is capable of delivering anesthetic and other agents to nasal cavities and is also capable of performing a variety of medical procedures for treatment of sinusitis. There is also a need for a sinus surgery device that is easier to maneuver inside the nasal passages to eliminate or lessen patient's discomfort and anxiety during the procedure.

SUMMARY OF THE INVENTION

Accordingly, it is an object of the present invention to provide a method for localized delivery of various therapeutic and/or diagnostic agents to nasal cavities and tissues via a nested balloon catheter system to facilitate surgical treatment of sinusitis and other ear, nose and throat disorders.

It is another object of the present invention to provide a method of delivering various agents to nasal cavities that facilitates infusion of the agents into surrounding tissues.

It is yet another object of the present invention to provide a method of delivering various agents to nasal cavities that provides physiological feedback from which the intra-lumen diameter of the nasal cavity can be determined, and the pressure and flow supplied to the balloon can be adjusted accordingly.

It is a further object of the present invention to provide a method of delivering various agents to nasal cavities that provides visualization from within the bodily cavity.

It is also an object of the present invention to provide a method of dilating nasal passages via a nested balloon catheter system.

In order to overcome the deficiencies of the prior art and to achieve at least some of the objects and advantages listed, the invention comprises a method of localized delivery of a therapeutic and/or diagnostic agent to nasal tissue or cavities, including the steps of inserting a catheter into a nasal cavity, the catheter having an outer balloon having a wall with at least one opening therethrough and an inner surface, and an inner balloon at least partially disposed in the outer balloon, the inner balloon at least partially enclosing an inflation chamber and having an outer surface defining a space between the outer surface of the inner balloon and the inner surface of the outer balloon. The method further includes the steps of supplying the therapeutic and/or diagnostic agent to the space between the outer surface of the inner balloon and the inner surface of the outer balloon via a first lumen of the catheter, and inflating the balloon by supplying fluid to the inflation chamber via a second lumen of the catheter to urge the therapeutic and/or diagnostic agent out of the at least one opening in the wall of the outer balloon and into nasal tissue.

In some embodiments, the method further includes the step of directing the therapeutic and/or diagnostic agent to a localized area in the nasal cavity via at least one protrusion formed by at least one of an inner balloon wall and the outer balloon wall.

In certain embodiments, the therapeutic and/or diagnostic agent comprises an anesthetic. In additional embodiments, the therapeutic and/or diagnostic agent comprises a mucolytic agent. In further embodiments, the therapeutic and/or diagnostic agent comprises an antihistamine agent.

In some cases, the method further includes the step of heating at least one of the inner balloon and the outer balloon.

In certain advantageous embodiments, the method also includes the step of dilating a nasal passage by placing the inner and outer balloons in the passage and inflating the inner balloon such that the outer balloon contacts walls of the nasal cavity and dilates the cavity.

In some embodiments, the method further includes the step of mitigating bleeding in the nasal cavity by applying pressure to the cavity wall via the outer balloon.

In certain embodiments, the method also includes the step of visualizing the nasal cavity via an imaging device disposed in the catheter.

In some cases, the catheter further includes an irrigation device and a suction device disposed in the catheter and the method further includes the step of delivering irrigation fluid to the nasal cavity via the irrigation device and suctioning the irrigation fluid out of the nasal cavity via the suction device.

In certain embodiments, the catheter further includes a flexible steering member disposed at a distal end of the catheter and the method further includes the step of maneuvering the catheter through the nasal anatomy via the steering member.

In some embodiments, the wall of the outer balloon has an abrasive outer surface, and the step of inflating the inner balloon includes contacting tissue in the nasal cavity with the abrasive surface such that it abrades the tissue.

In certain advantageous embodiments, the step of delivering the therapeutic and/or diagnostic agent to tissue further includes inflating the inner balloon until the wall of the outer balloon contacts tissue in the nasal cavity.

In certain embodiments, the step of inflating the inner balloon includes supplying fluid thereto with a fluid source. In some of these embodiments, the method also includes the step of monitoring at least one patient vital sign via a monitoring device and controlling the pressure to which the inner balloon is inflated via the fluid source based at least in part on the monitored vital sign. In additional embodiments, the method further includes the step of monitoring at least one patient vital sign via a monitoring device and controlling the supply of the therapeutic and/or diagnostic agent via the fluid source based at least in part on the monitored vital sign. In further embodiments, the method also includes the step of repeatedly deflating and inflating the inner balloon in pulsed fashion by supplying fluid thereto via the fluid source. In yet further embodiments, the method further includes the step of evacuating fluid from the inflation chamber via the fluid source.

In some embodiments, the step of directing the therapeutic and/or diagnostic agent to the localized area in the nasal cavity includes supplying the agent to a channel defined by a first protrusion formed by the inner surface of the outer balloon and a second protrusion formed by the outer surface of the inner balloon.

In certain embodiments, the method also includes the step of measuring at least one characteristic of tissue in the bodily cavity via at least one sensor.

In some cases, the catheter further includes a distal balloon positioned distally of the inner and outer balloons and a proximal balloon positioned proximally of the inner and outer balloons, wherein the method further includes the step of inflating the distal and proximal balloons by supplying fluid thereto via at least one additional lumen of the catheter to create a chamber between the distal and proximal balloons, and wherein the step of delivering the therapeutic and/or diagnostic agent includes delivering the agent to the chamber.

In certain advantageous embodiments, the wall of the outer balloon has an outer surface comprising a mesh sleeve of elastic yarn. In some of these embodiments, the mesh sleeve is radiopaque.

In some cases, the agent is a combination of at least one therapeutic and/or diagnostic agent and at least one biomarker.

Other objects of the invention and its particular features and advantages will become more apparent from consideration of the following drawings and accompanying detailed description.

DETAILED DESCRIPTION OF THE INVENTION

Figure 1:
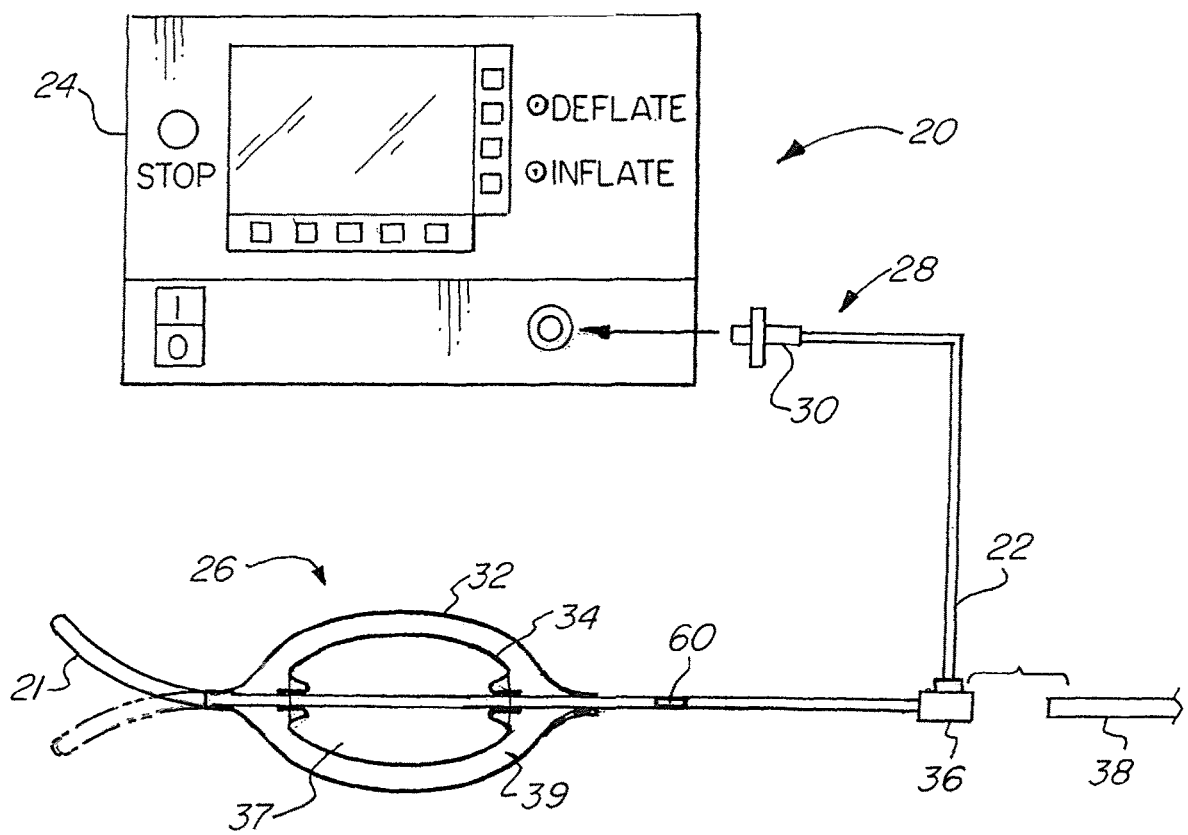
FIG. 1 is a schematic view of a balloon catheter system for delivering therapeutic and/or diagnostic agents in accordance with the invention.

The basic components of an exemplary embodiment of a balloon catheter system for localized delivery of a therapeutic and/or diagnostic agent to nasal tissues or cavities in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, the balloon catheter system (20) includes a catheter (22) and a fluid source (24). The catheter (22) has a suitable diameter and length to allow for its insertion into various nasal cavities and may be flexible, rigid or semi rigid. The catheter (22) may be made with any commercially available material, such as, for example, polyether amide (PEBA), Pebax® or polyurethane, that is flexible enough to allow the shaft to be safely inserted through the nasal passages such that it will bend instead of puncturing the passage walls, and at the same time is rigid enough such as it will maintain its shape as it is passed through the passages. In one advantageous embodiment, the catheter (22) consists of a coil wire made of any suitable material, such as stainless steel, and a coating made of polyethylene. A distal end of the catheter (22) preferably includes a safety tip (not shown) that, when the catheter (22) is inserted into a nasal cavity, will bend instead of puncturing the walls of the cavity.

Any suitable fluid source may be used in accordance with the present invention. In one advantageous embodiment shown in FIG. 1, the fluid source (24) is an electro-pneumatic pump having controls on the front thereof, from which a physician or assistant can control the system (as well as a remote control unit), such as that disclosed in U.S. Pat. No. 8,226,601 by Gunday et al., the specification of which is hereby incorporated by reference herein in its entirety. A proximal end (28) of the catheter (22) is connected to the pump (24) via a connection port (30). The port (30) is provided with any suitable connector, such as a luer connector, for connection to the pump. The pump (24) supplies a fluid, such as a gas, liquid, or mixture thereof, to the catheter (22). The pump (24) also includes a variety of capabilities for balloon identification, proper inflation/deflation of the balloons, and feedback measurements, many details of which are described in Gunday et al. In certain advantageous embodiments, the pump (24) further includes a vacuum source to evacuate fluid from the catheter (22).

In some embodiments, the catheter (22) includes a data device, which may, for example, be optical, RFID, flash memory, etc. As a result, the pump (24) is able to identify the type of catheter that is connected and read catheter characterization data (including pressure, volume, dimensions, etc.) included thereon, and then adjust its control accordingly based on user input.

The pump (24) also controls and regulates the pressure by monitoring and taking into account one or more vital signs of the patient, such as body temperature, heart rate, blood pressure, and respiratory rate. For example, in certain applications, it will be desirable to know the patient's inhalation and exhalation cycles in order to deliver the drug at the right time. Similarly, in certain cases, it will be important to measure the systolic and diastolic blood pressure, and at appropriate times, apply a pressure that exceeds the systolic pressure in order to facilitate extravasation of the drug. In certain embodiments, the electro-pneumatic pump (24) interfaces with an external monitoring device to obtain and monitor the patient vital signs to control the pressure to which the inner balloon is inflated and/or to control the supply of the therapeutic and/or diagnostic agent to the outer balloon. In other cases, the monitoring device is located in the pump (24).

In an advantageous embodiment, the catheter (22) also includes a connection port (36) for insertion of an imaging device (38). The structure and operation of the imaging device is described in more detail below.

Figure 2:
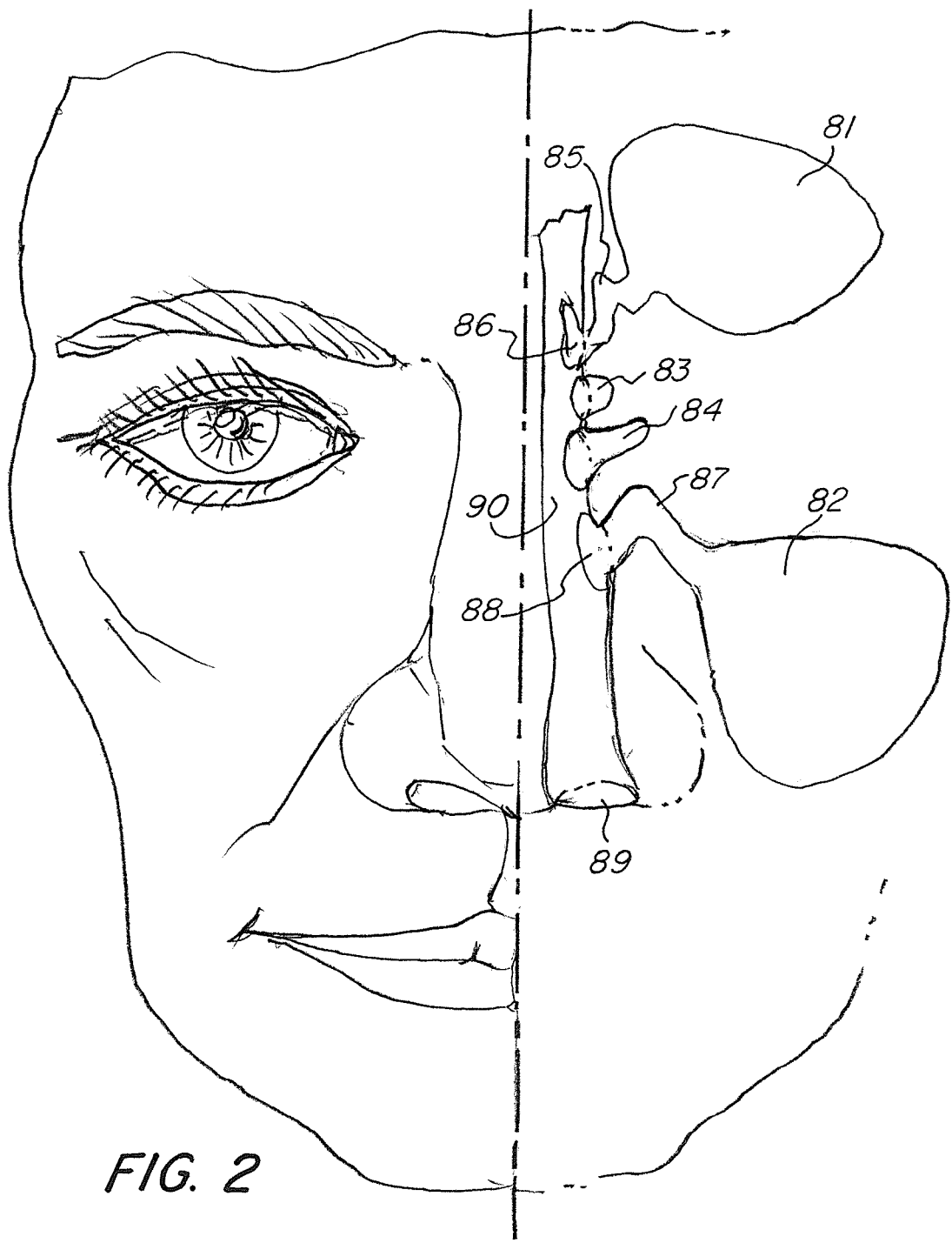
FIG. 2 is a schematic view of various nasal passages and cavities.

A human skull contains a series of cavities known as paranasal sinuses that are connected by passageways. As shown in FIG. 2, the paranasal sinuses include frontal sinuses (81), ethmoid sinuses (83), sphenoid sinuses (84), and maxillary sinuses (82). The paranasal sinuses are lined with mucous-producing mucosal tissue and ultimately open into the nasal cavity. Normally, mucus produced by the mucosal tissue slowly drains out of each sinus through a sinus passage into an opening known as an ostium. For example, FIG. 2 shows a frontal sinus ostia (85) leading to a frontal sinus ostia opening (86) and a maxillary sinus ostia (87) leading to a maxillary sinus ostia opening (88). If the mucosal tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e. g., a sinus infection or sinusitis).

Typically, during a sinus surgery, a working device, such as a guiding catheter, working channel or an endoscope, is inserted into one of the patient's nostrils (89), through the nasal passage (90) and is then extended into one of the sinus cavities, such as, for example, frontal sinus (81) or maxillary sinus (82). In order to position the device in the sinus cavity, the device has to be manipulated through tortuous sinus ostia passages (85, 87). Sinus surgery devices known in the art typically have either a fixed bent shape at their distal end or a malleable distal end that can be shaped before introduction into the sinus ostia passages. When the devices reach the ostia passages, the bent distal end is rotated to allow passage of the device into the curved ostia. However, this limits the ability of the surgeon to maneuver the devices through various shapes of the sinus passages and often causes significant pain and bleeding to the patient.

The balloon catheter (20) of the present invention solves this problem by incorporating a flexible steering member (21) disposed at a distal end of the catheter, as shown in FIG. 1. The steering member is used to maneuver the catheter (22) through the nasal anatomy, as will be discussed in more detail below. One exemplary embodiment of the steering member is disclosed in U.S. application Ser. No. 14/507,556 by Gerrans et al., the disclosure of which is incorporated herein in its entirety. In this embodiment, the steering member (21) has a generally cylindrical body with a plurality of arcuate slits cut through the wall of the steering member, which allow the member to flex in different directions. The member further includes at least two channels that accommodate pull wires coupled to an actuator positioned at a proximal end of the catheter (22) for actuation of the member.

An additional exemplary embodiment of the steering member is disclosed in U.S. Publication No. 2012/0226103 by Gunday et al., the disclosure of which is incorporated herein in its entirety. In this embodiment, the steering member (21) includes a plurality of tapered steering lumens disposed therein. A fluid source connected to the lumens provides fluid to the lumens to selectively increase diameters of the steering lumens, which causes the steering member to bend in a particular direction. The steering member may also be provided with piezo-electric elements to further assist in streering the member.

It is understood that any other suitable design of the steering member and its actuation mechanism may be used in accordance with the present invention.

The balloon catheter system (20) also includes a double balloon construct positioned at a distal end (26) of the catheter (22). The double balloon construct consist of an outer balloon (32) and an inner balloon (34) at least partially disposed in the outer balloon. The balloons (32, 34) may be made of latex, Yulex, polyethylene, nylon or other suitable material, and may come in a variety of sizes and diameters, which allow the nested balloon catheter system (20) to be used in bodily cavities of various diameters and dimensions, such as large and small bronchial branches, sinuses, and blood vessels, having different types of tumors and tissues to be treated. In certain embodiments, the balloon surfaces include an inert coating, such as a biocompatible lubricant, that facilitates the flow of drugs and agents between the balloons.

The outer balloon (32) has a wall with at least one opening therethrough and an inner surface. The inner balloon (34) at least partially encloses an inflation chamber (37) into which fluid is supplied from the fluid source (24) to inflate the inner balloon (34). In some embodiments, the fluid source (24) evacuates fluid from the inflation chamber (37) to facilitate faster deflation of the inner balloon (34). An outer surface of the inner balloon (34) defines a space (39) between the inner surface of the outer balloon (32) and the outer surface of the inner balloon (34). The therapeutic and/or diagnostic agent is supplied to the space (39) and is then delivered to tissue through the openings in the wall of the outer balloon (32).

In some advantageous embodiments, the outer balloon (32) has a textured outer surface that acts as a gripping surface for attachment to nasal tissues, such as walls of the nasal passages, to anchor the balloon catheter (20) in the nasal cavities/passages. In additional advantageous embodiments, the outer surface of the outer balloon (32) has a micro-abrasion surface intended to abrade the nasal tissue to stimulate bleeding and to instigate leukocyte extravasation and perpetuate fluid extravasation when volumetric pressure or force is applied to the abraded surface of the nasal tissue to neutralize hemodynamic shear forces and further stimulate the extravasation process and associated cellular absorption of the diagnostic and/or therapeutic agents into the tissues.

In the embodiments wherein the outer balloon (32) has the abrasive and/or gripping surface, the outer surface of the outer balloon (32) includes a fiber mesh affixed to the surface during or after the molding process, which produces outwardly-facing protrusions that assist in gripping tissue in the bodily cavity and/or that optimize the abrasion capability of the balloon. The fiber mesh may be made of lycra, polyurethane, nylon, nylon coated with other materials such as cotton, composite springs, or other appropriate material. In other embodiments, dimensional surface structures or inflatable sinuses that are encapsulated in the surface substrate of the outer balloon (32) may be used to produce the surface protrusions.

In an advantageous embodiment of the balloon catheter (20), the inner balloon (34) and the outer balloon (32) are not bonded together. The inner balloon (34) is bonded at one end to the catheter (22), and then is pulled over the bonded end. The same is done at the other end, such that the inner balloon (34) curves inward towards the bonded parts when inflated, as shown in FIG. 1. The outer balloon (32) is pulled away from the bonded parts such that the outer balloon (32) curves outwards upon inflation, as also shown in FIG. 1. Such design creates extra space between the inner balloon (34) and the outer balloon (32) for accommodating the therapeutic and/or diagnostic agent.

In certain advantageous embodiments, at least one of the balloons (32, 34) includes imaging markers, such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloons (32, 34). Similarly, the balloon or balloon mesh may include radiopaque material, such as a mesh made of yarn having radiopaque iron fibers.

The balloon catheter of the present invention also includes at least one sensor for measuring at least one characteristic of tissue. The sensor (60) may be positioned in a catheter lumen or on the outside of the catheter (22) adjacent the outer and inner balloons (32, 34), as shown in FIG. 1. It is understood that the sensor may also be positioned at any other desired location along the catheter (22). The sensor (60) measures various characteristics of tissue or surrounding environment such as temperature, pressure, density, and concentration of various elements, such as oxygen, carbon, etc. Two or more sensors may be used in accordance with the present invention to measure different tissue characteristics. The sensors are positioned at different locations along the catheter (22). The measurements from the sensors are helpful in obtaining information about tissues undergoing treatment and monitoring interaction of the delivered agents with the tissue.

Figure 3:
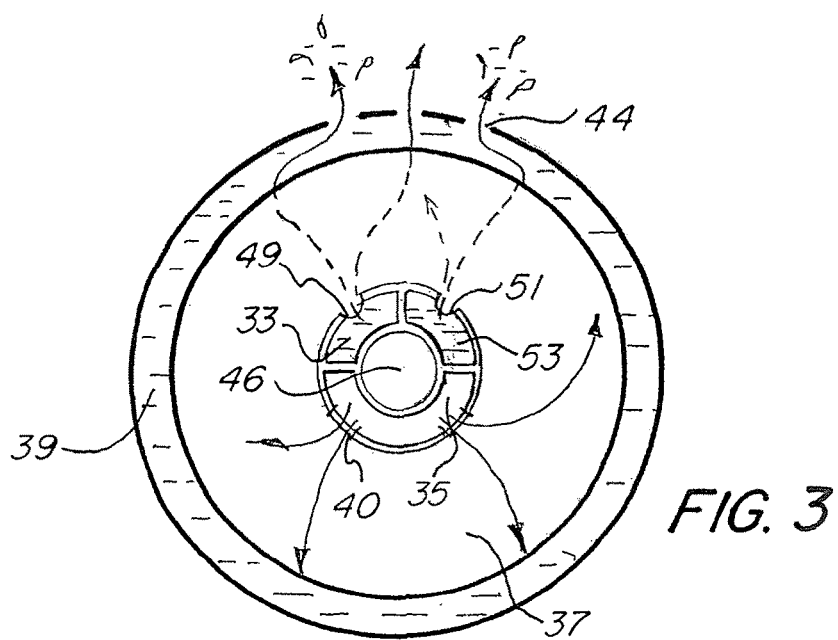
FIG. 3 is a cross-sectional view of the catheter assembly of FIG. 1.

The catheter (22) includes a first lumen (33) and a second lumen (35), as shown in FIG. 3. The first lumen (33) is in fluid communication with the space (39) between the inner surface of the outer balloon (32) and the outer surface of the inner balloon (34) via an opening (49). The first lumen is used to supply the therapeutic and/or diagnostic agent to the space (39), and then through the openings (44) in the wall of the outer balloon (32) into tissue in the nasal cavity. The second lumen (35) is in fluid communication with the inflation chamber (37) in the inner balloon (34) via at least one opening (40) in the catheter (22). The second lumen (35) is used to supply fluid from the fluid source (24) to the inflation chamber (37) to inflate the inner balloon (34).

The catheter (22) further includes a center lumen (46), which can be used to deliver any number of things to assist insertion and positioning of the balloon catheter system (20) within the nasal cavities and to carry out various medical procedures. It should be noted that additional lumens may be provided in the catheter (22) for introduction of various medical instruments to carry out various diagnostic or therapeutic procedures. The center lumen (46) can also be used as a bypass channel to allow bodily fluids, such as blood or mucus, to flow through the balloon catheter. Though not all are shown, the referenced lumens each terminate and are accessible at the proximal end of the catheter (26).

In an advantageous embodiment, an imaging device disposed in one of the lumens of the catheter (22) can be used to help position the inner and outer balloons at the proper location. For example, the lumen (33) that delivers the therapeutic and/or diagnostic agent may be large enough to also accommodate the imaging device, such that the imaging device can exit one of the openings (49), through which the agent is delivered into the space (39) between the balloons. In this embodiment, the wall of the outer balloon (32) is transparent such that the imaging device can view the surrounding tissue through the wall.

In other embodiments, both the inner and outer balloons (32, 34) are transparent, and the imaging device can be introduced via the lumen (35), through which fluid is supplied to the inflation chamber (37) to inflate the inner balloon (34), out one of the openings (40) and into the inner balloon (34) in order to view the surrounding area through the transparent wall of the inner and outer balloons. Alternatively, an additional lumen can be provided in the catheter (22) to accommodate the imaging device, such as the center lumen (46), and this lumen can connect to an opening leading to the inside of the inner balloon (34) or to the space (39) between the inner balloon (34) and the outer balloon (32). In additional embodiments, this lumen can connect to an opening in the wall of the catheter outside of the balloons.

In some advantageous embodiments, the distal end of the catheter (22) includes a transparent membrane made out of any suitable material. The imaging device is extended through one of the lumens of the catheter to the membrane, which allows for visualization of the area ahead of the catheter (22). In this way, the physician can be provided with illuminated light and direct visual feedback of the area ahead of the balloon catheter, along the sides of the balloons, and/or behind the balloons.

Figure 4A:
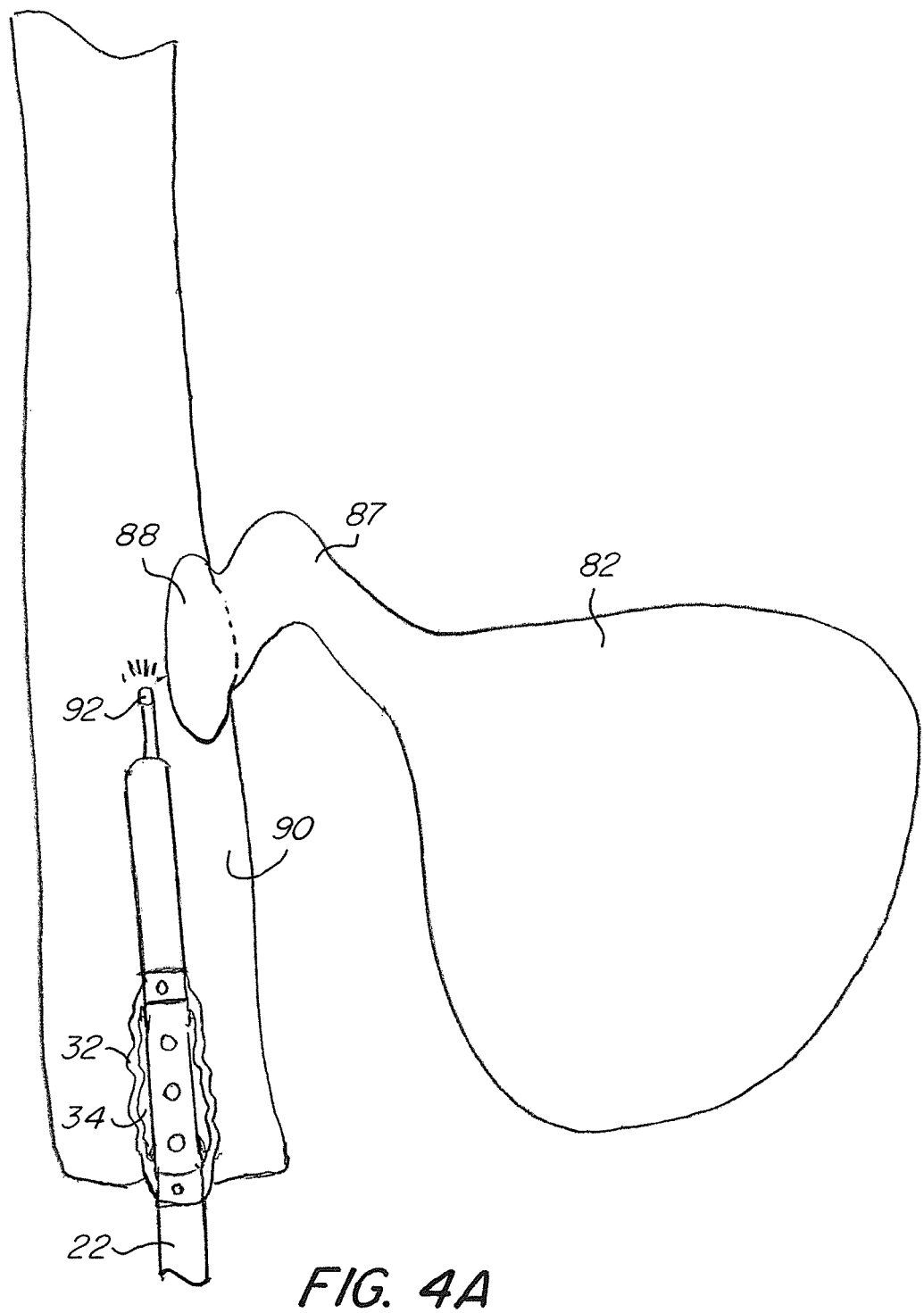
FIGS. 4A-4D illustrate a stepwise method of operating the balloon catheter system of FIG. 1 in a patient's nasal anatomy.
Figure 4B:
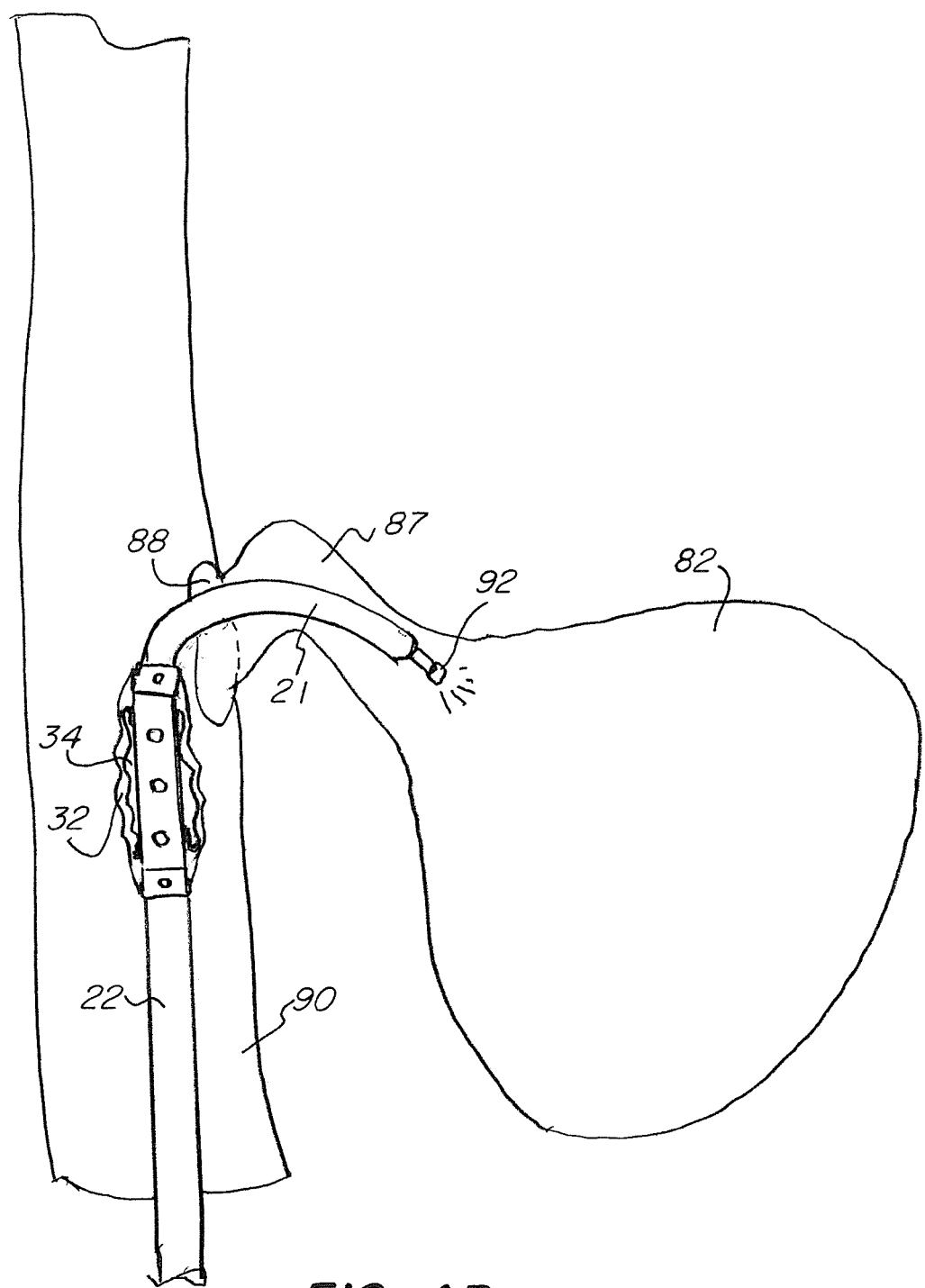

In other advantageous embodiments, such as illustrated in FIGS. 4A and 4B and further discussed below, the lumen of the catheter (22), in which the imaging device is disposed, has an opening at a distal end, and the imaging device is extended out of the opening to visualize tissue in front of the nested balloon catheter system (20). In this embodiment, the catheter (22) can also be provided with a cleaning device at the distal tip for cleaning the imaging device. The cleaning device is made with any suitable type of material, such as textile bundle or flexible flaps of material, and is affixed to an inner surface of the catheter (22) adjacent to the opening at the distal end. The imaging device is cleaned by moving it back and forth through the cleaning device, thus wiping a lens of the imaging device.

The imaging device can be any device suitable for viewing the target area, such as a coherent fiber bundle or appropriate optical element and lens assembly in conjunction with an imaging sensor (e.g., CMOS, CCD), having a sufficiently small outer diameter, such as, for example, 0.75 mm-1.5 mm. In some cases, the imaging device has a pre-shaped distal tip that enables it to easily extend through one of the aforementioned openings. The distal tip of the imaging device is preferably flexible such that it can be translated linearly or rotationally, thereby allowing for 360° visualization of the surrounding area. In additional embodiments, the distal section of the imaging device is steerable such that it may be bent to different angles to facilitate insertion of the imaging device into tortuous nasal passages and to enable imaging of nasal anatomy at different angles. Any suitable steering mechanism, including the mechanisms described above with respect to the flexible steering member (21) of the catheter (22), may be used.

FIGS. 4A-4D illustrate a stepwise operation of the balloon catheter system (20) in a nasal cavity. The catheter assembly (22) is first inserted into one of the nostrils in a patient's nose and is extended into the nasal passage (90), as shown in FIG. 4A. An imaging device (92) is extended out of the opening at the distal end of the catheter (22) to assist in insertion of the catheter into a nasal cavity. It is understood that, in some embodiments, a working channel may be inserted into the nasal passage first, and then the catheter assembly (22) is inserted through the working channel. In additional embodiments, a steerable guide wire with or without an imaging device may be inserted into the nasal passage first, and then the catheter assembly (22) is inserted over the guide wire.

Next, the distal end of the catheter is brought to a maxillary sinus ostia (87) leading to a maxillary sinus ostia passage (88). The flexible steering member (21) of the catheter (22) is steered into the opening under the guidance of the imaging device (92) and the double balloon construct (32, 34) is advanced into the ostia passage (88) until is it positioned at a desired location within the ostia, as shown in FIG. 4B. The flexible steering member (21) can be actuated in different directions to facilitate insertion of the catheter through several bends in the ostia passage.

Figure 4C:
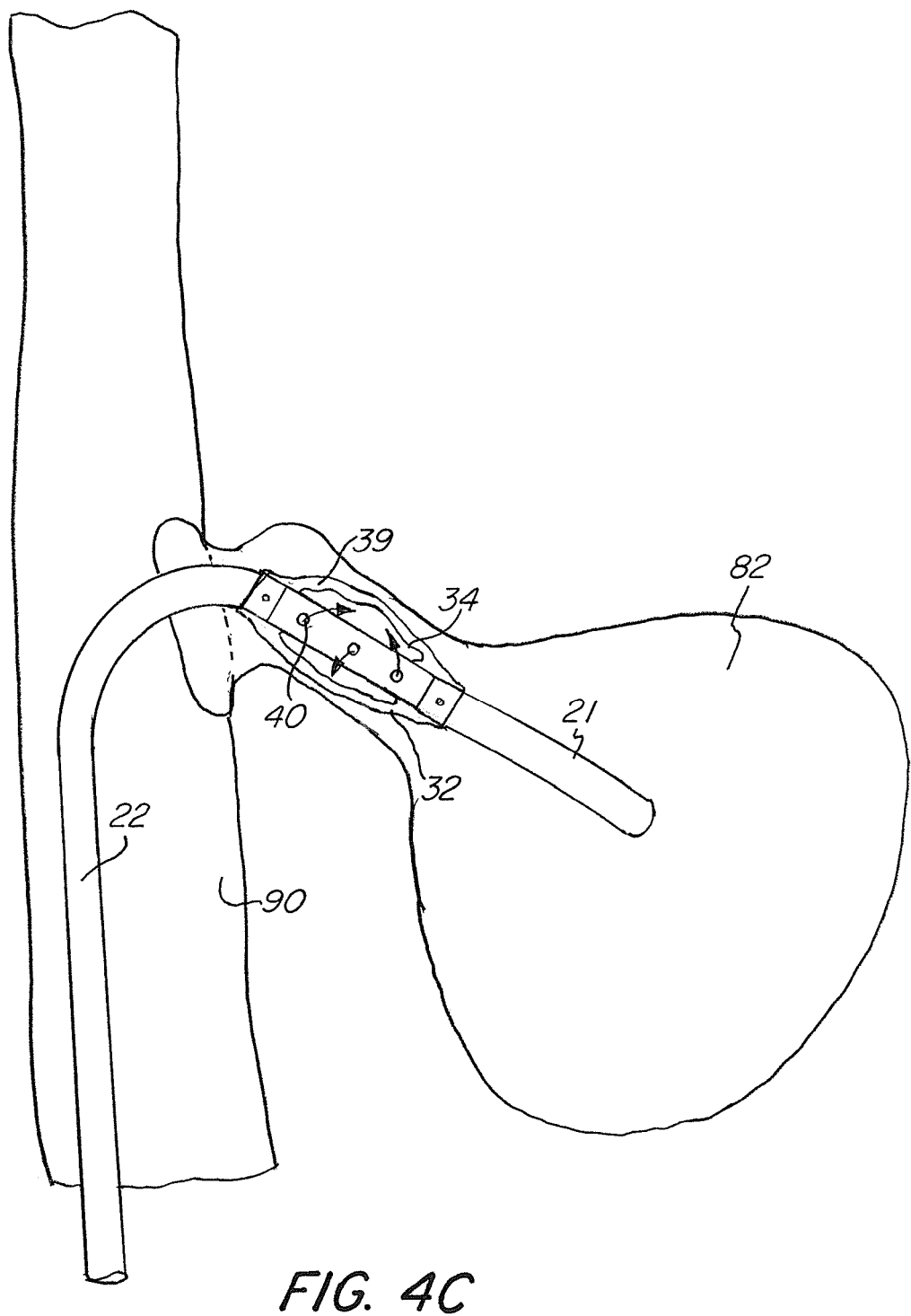

Once the catheter (22) reaches the desired position in the ostia passage (87), fluid is supplied to the inflation chamber (37) via the lumen (35) in the catheter (22) through the plurality of openings (40) to inflate the inner balloon (34), as illustrated in FIG. 4C. It should be noted that, although the plurality of openings (40) in the catheter (22) are illustrated in this figure, one opening is sufficient to supply fluid to inflate the inner balloon (34).

Figure 4D:
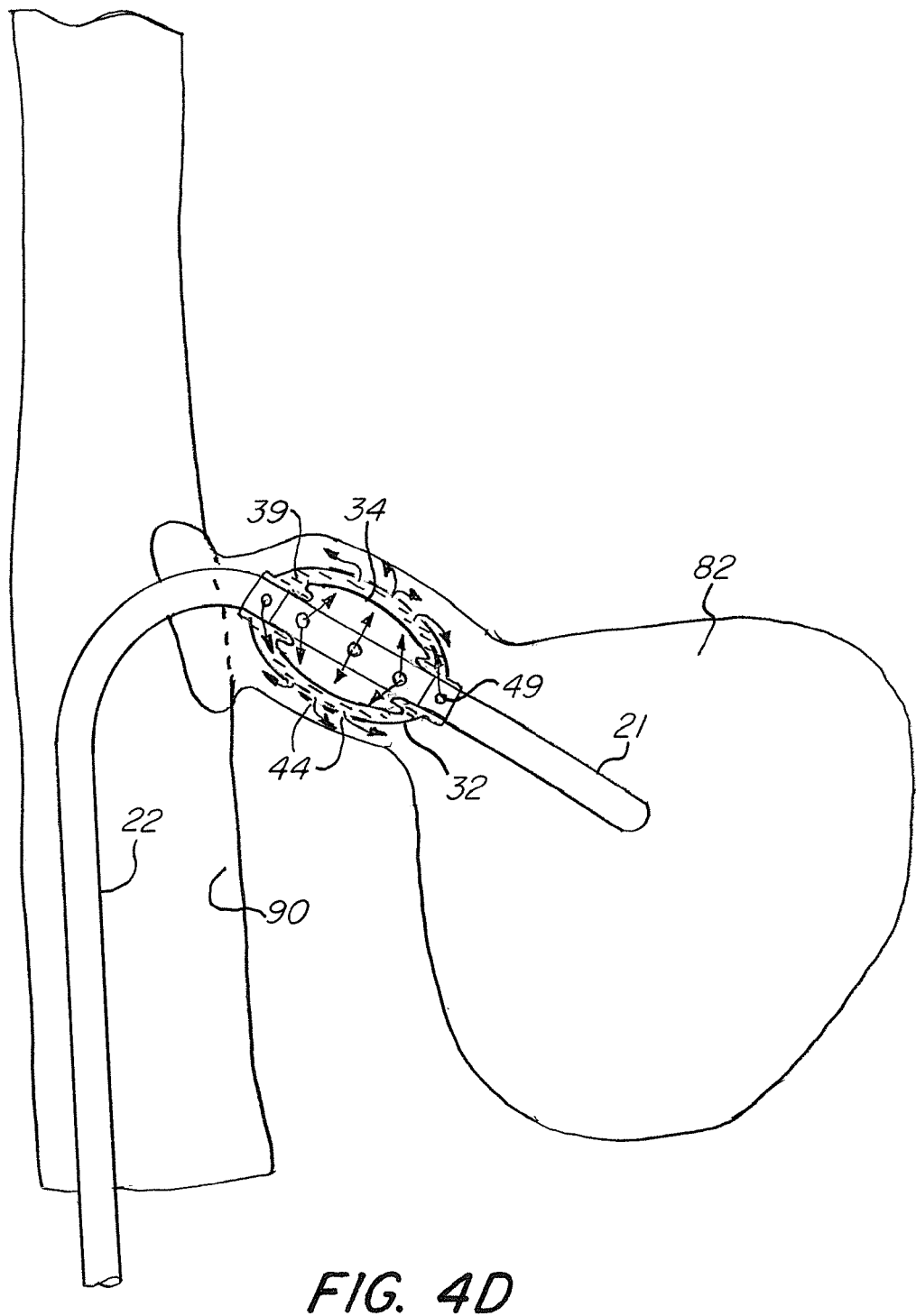

As the inner balloon (34) becomes inflated, a therapeutic and/or diagnostic agent is supplied via the lumen (33) in the catheter (22) to the space (39) between the inner balloon (34) and the outer balloon (32). The agent is supplied through the openings (49) in the catheter (22) positioned within the space (39), such that the agent fills the space (39) between the balloons. As illustrated in FIG. 4D, the inner balloon (34) is continuously inflated and the therapeutic and/or diagnostic agent is urged out of the openings (44) in the wall of the outer balloon (32) and into the surrounding nasal tissue.

In the embodiment shown in FIG. 4D, the inner balloon (34) is only partially inflated, such that the agent is pushed out of the openings in the outer balloon (32) into a space between the nasal tissue and the wall of the outer balloon (32). This may be desirable in order to minimize pressure exerted on the nasal passages and thus, alleviate patient's pain and anxiety. However, it is understood that, in some cases, the inner balloon (34) can be fully inflated, such that the wall of the outer balloon (32) is pressed against the nasal tissue (42), which facilitates the absorption of the therapeutic and/or diagnostic agent into the tissue.

In some embodiments, the outer balloon (32) is also inflated by supplying fluid thereto by the fluid source (24) via an additional lumen in the catheter (22), separate from the lumen (33) used to supply the therapeutic and/or diagnostic agent. In these embodiments, the outer balloon (32) can be inflated such that the wall of the outer balloon (32) presses against the tissue (42), and then the agent is delivered through the openings (44) into the tissue. This way, the agent can be delivered to a more precisely targeted area of the tissue. Additionally, the inflation of the outer balloon (32) can assist in anchoring the balloon assembly within the nasal cavity during the drug delivery process.

Although FIG. 4A-4D show the method of using the balloon catheter system (20) in the maxillary sinus ostia, it is understood that the same method can be applied to any other nasal cavities or passageways, including the frontal sinuses, ethmoid sinuses, and sphenoid sinuses.

In some embodiments, the balloon catheter system (20) may include a secondary inflatable balloon positioned distally or proximally of the double balloon construct (32, 34). The secondary balloon is used to anchor the balloon catheter (20) inside a nasal cavity or passage. An outer wall of the secondary balloon may have textured surface to facilitate gripping of the balloon to the nasal passage or cavity walls. Once the catheter (22) is inserted into the nasal cavity or passage and positioned at a desired location, the secondary balloon is inflated first to anchor the catheter, and then the therapeutic and/or diagnostic agent is delivered via the inner/outer balloon construct (32, 34). The secondary balloon may also act to occlude the nasal passage/cavity, such that the therapeutic and/or diagnostic agent is contained therein such that it does not leak out of the cavity/passage, which may be undesirable.

Any of various agents useful in therapeutic application can be delivered in the above described manner. For example, the balloon catheter of the present invention can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Examples of diagnostic or therapeutic agents are contrast agents, a pharmaceutically acceptable salt or dosage form of an antimicrobial agent (e.g., antibiotic, antiviral, anti-parasitic, antifungal, etc.), an anesthetic agent, an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, or immunomodulator), an allergen or another substance that causes secretion of mucous by tissues, anti-proliferative agents, hemostatic agents to stop bleeding, cytotoxic agents (e.g. alcohol), biological agents such as protein molecules, stem cells, genes or gene therapy preparations etc.

Antimicrobial agents can include, but are not limited to, acyclovir, amantadine, amikacin, gentamicin, tobramycin, amoxicillin, amphotericin B, ampicillin, sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clavulanate, clotrimazole, ciprofloxacin, clarithromycin, clindamycin, dapsone, dicloxacillin, doxycycline, erythromycin, fluconazole, foscarnet, ganciclovir, atifloxacin, imipenem, cilastatin, isoniazid, itraconazole, ketoconazole, metronidazole, nafcillin, nystatin, penicillin, penicillin G, pentamidine, piperacillin, rifampin, quinupristin-dalfopristin, ticarcillin, trimethoprim, sulfamethoxazole, tazobactam, valacyclovir, vancomycin, mafenide, silver sulfadiazine, mupirocin, nystatin, triamcinolone, butoconazole, miconazole, tioconazole, and combinations thereof. Anti-inflammatory agents can include, but are not limited to, beclomethasone, flunisolide, fluticasone proprionate, triamcinolone acetonide, budesonide, loterednol etabonate, mometasone, aclometasone, desonide, hydrocortisone, betamethasone, clocortolone, desoximetasone, fluocinolone, flurandrenolide, prednicarbate, amcinonide, desoximetasone, diflorasone, fluocinolone, fluocinonide, halcinonide, clobetasol, salicylic acid derivatives, aspirin, sodium salicylate, choline magnesium trisalicylate, salsalate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, piroxicam, meloxicam, nabumetone, rofecoxib, celecoxib, etodolac, nimesulide and combinations thereof.

Exemplary decongestants include, but are not limited to, pseudoephedrine, xylometazoline, oxymetazoline, phenylephrine, epinephrine, and combinations thereof.

In some advantageous embodiments, the agent comprises an anesthetic agent. The anesthetic agent is delivered to nasal passages in the manner described above to provide local pain relief such that further surgical procedures may be performed on the passages, such as, for example, dilation of the sinus ostia passage. Any desirable anesthetic agent may be delivered by the method of the present invention. Some examples include, but are not limited to, cocaine, lidocaine, tetracaine, and combinations thereof.

In additional embodiments, the balloon catheter system is used to deliver a mucolytic agent. As described above, when a patient has a sinusitis condition, the mucosal tissue in the nasal passages becomes inflamed, which causes accumulation of mucus in the passageways, thereby blocking them. Mucolytic agents are designed to help loosen and clear the mucus from the nasal passages by breaking up the sputum to facilitate removal of the blockages in the passageways. Such mucolytic agents include, but are not limited to, cromolyn, nedocromil, azelastine, diphenhydramine, loratidine, acetylcysteine, bromheksin, guiafenesin, and combinations thereof. The mucolytic agents are delivered to the nasal passages by the balloon catheter system to help loosen the mucus such that it can be more easily drained or flushed from the passages to relieve the sinusitis condition.

In further embodiments, the system delivers an antihistamine agent. The antihistamine agents, or histamine antagonists, help to prevent many of the symptoms of an allergic reaction in the nose (i.e. rhinitis), such as itching, runny nose and sneezing. The antihistamines work by blocking histamine attachment to histamine receptors in the brain, which prevents increased vascular permeability that leads to runny nose. Any type of antihistamine agents may be delivered by the method of the present invention, including but not limited to, acrivastine, azelastine, bilastine, brompheniramine, buclizine, bromodiphenhydramine, carbinoxamine, cetirizine, cyclizine, chlorpheniramine, chlorodiphenydramine, clemastine, cromolyn, cyproheptadine, desloratadine, dexbrompheniramine, dexchlorpheniramine, dimenhydrinate, dimetindene, diphenhydramin, doxylamine, ebastine, embramine, fexofenadine, hydroxyzine, levocetirizine, loratadine, nedocromil, olopatadine, phenindamine, pheniramine, phenyltoloxamine, promethazine, pyrilamine, rupatadine, tripelennamine, triprolidine, and combinations thereof.

In yet further embodiments, the system of the present invention delivers an osteolytic agent. The osteolytic agents cause breakdown of bone tissue in the body or osteolysis. This can occur, for example, by removal of calcium from the bone tissue, which causes dissolution of the bone. As described above, in patients suffering from a chronic or recurring sinusitis, it is desirable to enlarge the sinus ostia passages and remove obstructions in these passages to relieve the symptoms of sinusitis. In order to do that, some surgical procedures involve breakage or resection of the bone tissue. The delivery of osteolytic agents to the nasal passages facilitates removal of the bone tissue.

An exemplary anti-cholinergic is ipratropium bromide.

Diuretics can include, but are not limited to, furosemide and/or hyperosmolar agents such as sodium chloride gel or other salt preparations.

In certain applications, it may be desirable to locally deliver in a similar manner agents that will facilitate photodynamic therapy. Likewise various forms of energy can be delivered locally, including laser, microwave, RF, cryogenic, and thermal energies.

Various agents may also be employed to assist in making diagnostic observations or monitoring procedures. For example, in some advantageous embodiments, the above described method may be used to deliver a contrast agent that allows or improves visualization via one or imaging modalities, which can be used to image the extravasation of the agent into the surrounding tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one can visually identify the extravasation depths and/or discern the requisite volumetric pressure, force, temperature, frequency and/or time to achieve efficacious delivery of the therapeutic agent to the desired depth of penetration at the intended treatment site.

As described above, in certain advantageous embodiments, the wall of the outer balloon (32) has an abrasive surface. In these embodiments, the inner balloon (34) is first fully inflated, such that the abrasive surface of the outer balloon (32) abrades the tissue to stimulate a flow of leukocytes to the target tissue site, and then the agent is delivered to tissue through the openings in the outer balloon (32). This stimulates extravasation and associated cellular absorption of the diagnostic and/or therapeutic agent into the tissue. Alternatively, the agent is first urged into tissue by inflation of the inner balloon (34), and then the inner balloon is repeatedly inflated and deflated to abrade the tissue with the abrasive surface of the outer balloon (32).

In further embodiments, after the therapeutic and/or diagnostic agent is urged out of the openings (44) in the outer balloon (32), the pump (24) supplies fluid to the inflation chamber (37) in pulsed fashion to repeatedly inflate and deflate the inner balloon (34). This causes a change in volumetric pressure exerted on a nasal lumen wall to neutralize hemodynamic shear forces and to stimulate extravasation of the therapeutic agent into tissue. As explained above, the pump can apply controlled pressure that is synchronized with the patient's vital signs.

The catheter (22) can have multiple lumens to supply therapeutic agents to the space (39) between the inner and outer balloons (32, 34), which allows for delivery of multiple agents separately, as may be desired when using two different pharmaceuticals that should not be mixed until just before being extravasated into nasal tissue. For example, as shown in FIG. 3, the catheter (22) can include two delivery channels (33) and (51), each supplying a different agent via the openings (49) and (53) respectively. Likewise, one may need to deliver one medicinal agent, such as an anesthetic, at the beginning of the procedure, and another medicinal agent, such as mucolytic or antihistamine agent, at a later time during the procedure. In case where it is desirable to deliver two incompatible agents separately to prevent contamination, the space (39) between the balloons can be divided into several compartments, with each lumen leading to an opening into a separate compartment for delivery of a particular agent. Similarly, one may wish to deliver a second agent at a slightly different location than the first agent, which can be accomplished by providing two separate compartments between the balloons, for example one at the distal end of the balloons and the other at the proximal end of the balloons, and delivering each agent to tissue adjacent to each of the compartments.

Figure 5:
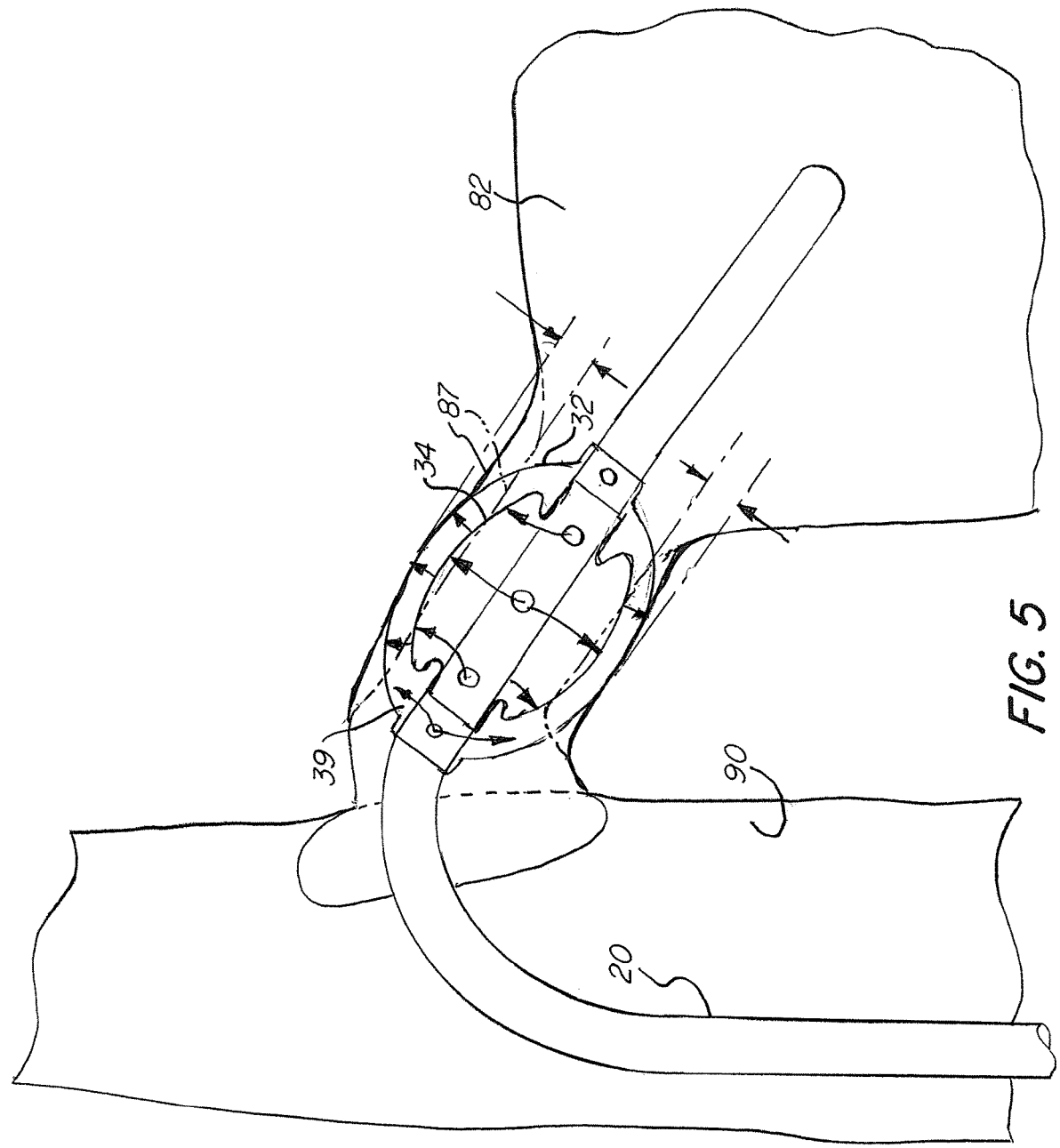
FIG. 5 is a partially exposed isometric view of the catheter assembly of FIG. 1, being used to dilate a nasal passage.

In some embodiments, the balloon catheter system (20) is used to dilate the sinus openings to relieve symptoms of sinusitis. As shown in FIG. 5, once the double balloon construct in brought into the sinus passageway (87), the inner balloon (34) is inflated such that the wall of the outer balloon (32) comes into contact with the walls of the ostia passage (87). The continued inflation of the inner balloon (34) causes the outer balloon (32) to exert pressure on the ostia passage walls, which in turn causes enlargement of the sinus passage (87) to allow the sinus cavity (82) to drain better. As described above, the outer balloon (32) can also be inflated to exert pressure on the cavity walls. In some embodiments, as described above, the pump (24) supplies fluid to the inflation chamber (37) in pulsed fashion to repeatedly inflate and deflate the inner balloon (34), which facilitates more gradual and gentle dilation of the sinus passage (87).

The dilation step is preferably preceded by the step of delivering an anesthetic agent to the nasal tissue to numb it to relieve patient's pain during this step. Other agents, e.g. antihistamine and/or mucolytic agent, may also be delivered prior to the step of dilating the ostia opening and/or after the dilation step.

As also described above, in some embodiments, the outer wall of the outer balloon (32) has an abrasive surface such that it abrades and resects tissue when the balloons are inflated. This abrasion/resection of tissue in the ostia passages helps to dislodge obstructions to further open up the passages. The repeated inflation and deflation of the inner balloon (34) in pulsed fashion also facilitates gradual and less traumatic resection of obstructions in the ostia passages.

In additional embodiments, a therapeutic agent may be delivered through openings (44) in the outer balloon (32) simultaneously with the inflation of the inner balloon (32) to dilate the ostia passage (87). For example, a mucolytic agent may be delivered simultaneously with the dilation of the ostia passage to further facilitate dislodging and clearing up of the mucus obstructions in the passage. Additionally, hemostatic agents may be delivered simultaneously with the dilation and/or abrasion of the ostia passage to prevent or mitigate bleeding caused during these procedures.

Furthermore, in some embodiments, the possible bleeding caused by the procedures performed in the ostia passage or nasal cavity is mitigated by the double balloon construct (32, 34) itself. The inner balloon (34) and/or outer balloon (32) is inflated such that the wall of the outer balloon (32) comes into contact with the walls of the ostia passage (87), and the continued inflation of the inner balloon (34) and/or outer balloon (32) causes the outer balloon (32) to exert pressure on the ostia passage walls. This applied pressure mitigates bleeding from the ostia passage walls, thereby making the procedure less traumatic to the patient.

In further embodiments, the inner and/or outer balloons (32, 34) may be supplied with heated or cryogenic fluid. For example, the inner balloon (34) is inflated by supplying heated or cryogenic fluid thereto, such that tissue in the nasal passages and cavities may be heated or cooled with the balloons. Additionally, heated or cryogenic fluid may be supplied to the outer balloon (32) and delivered to tissue through the openings (44) in the outer balloon (32). The heated or cryogenic fluid may assist with various things, such as mitigation of bleeding, dislodgement of obstructions in the ostia passages and dilation of the ostia passages.

Figure 6:
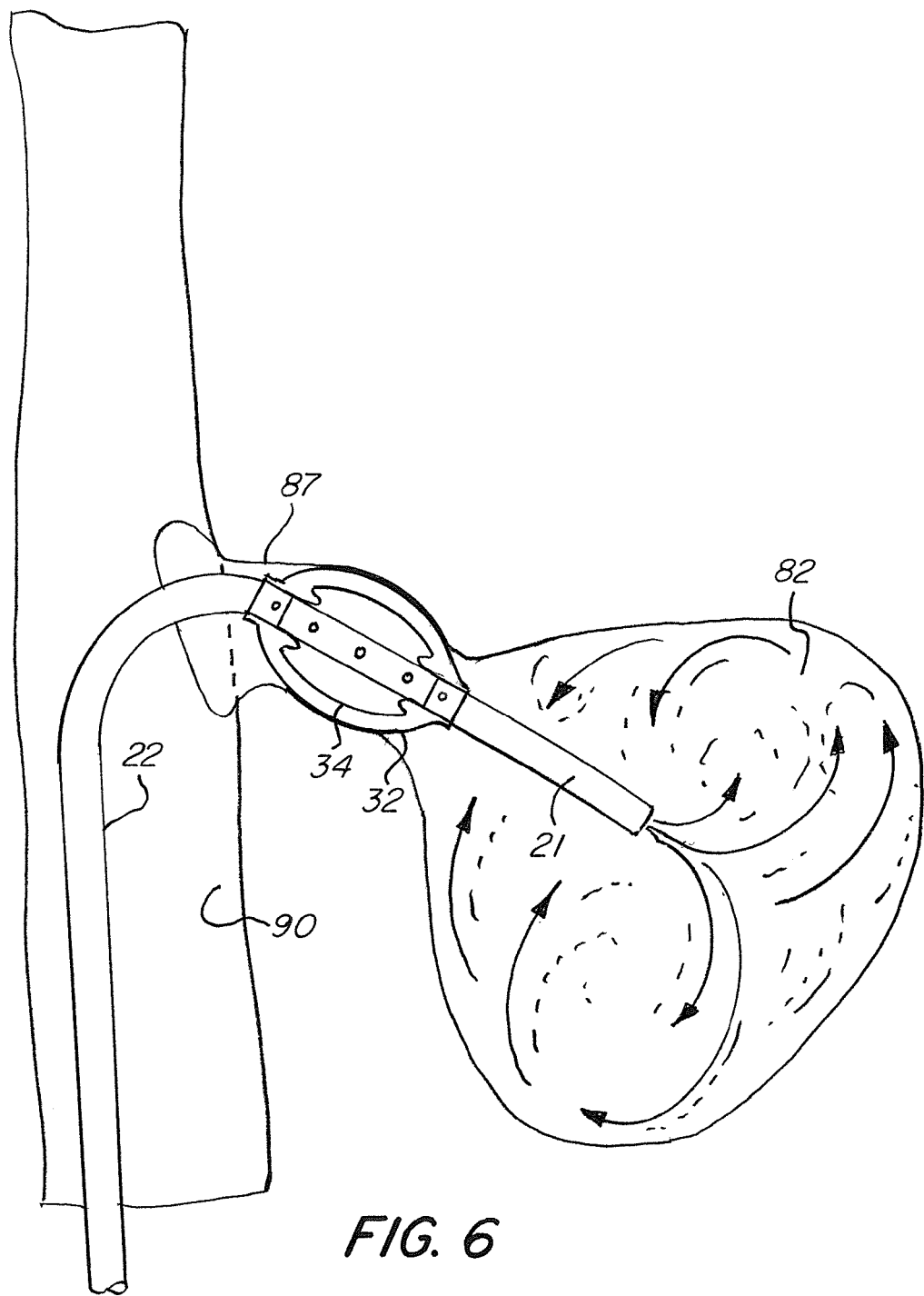
FIG. 6 is a partially exposed isometric view of the catheter assembly of FIG. 1, with an irrigation and suction feature.

As shown in FIG. 6, the balloon catheter system (20) also includes a suction and irrigation feature for providing lavage of the nasal cavities to facilitate removal of obstructions. In one exemplary embodiment illustrated in this figure, the distal end of the catheter (22) has an opening for delivering irrigation fluid to the nasal cavity (82). Any suitable irrigation fluid, such as saline, may be used. The irrigation fluid is delivered to the sinus cavity and is then suctioned out via the same or different opening in the distal end of the catheter (22). The irrigation fluid may be supplied to the distal end of the catheter (22) via the same lumen as is used to vacuum the fluid and other matter out of the nasal cavity. Alternatively, two separate lumens may be provided for supplying the irrigation fluid and vacuuming it out. Any suitable device, such as a syringe or a pump, may be used to supply and suction out the irrigation fluid.

Before the irrigation, lavage and/or suctioning of the nasal cavity is performed, the cavity (82) is isolated from the sinus passage (87) by inflating the inner/outer balloon construct (32, 34), as illustrated in FIG. 6. In additional embodiments, the double balloon construct (32, 34) itself may be used to deliver irrigation fluid, which is then vacuumed out via the opening in the distal end of the catheter (22). In these embodiments, the secondary balloon positioned proximally of the double balloon construct may be used to isolate the nasal cavity being lavaged from the nasal passage leading to the cavity.

The method of the present invention presents many advantages over the known sinuplasty procedures because the entire procedure, including delivery of an anesthetic and other drugs, dilation of the ostia passage, mitigating of bleeding, irrigation/lavage of the sinus cavity and/or other steps, are performed by the same device, without the need of introducing multiple medical tools into the patient's nose. This makes the procedure much faster and simpler, and also alleviates patient's pain and anxiety during the procedure.

Figure 7:
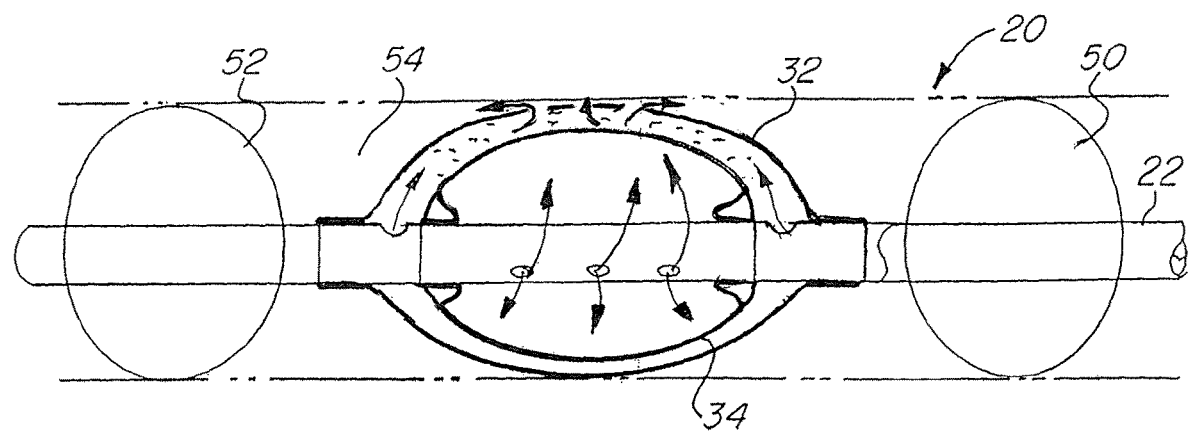
FIG. 7 is a partially exposed, isometric view of another embodiment of the catheter assembly of FIG. 1, positioned in a nasal cavity.

FIG. 7 illustrates another embodiment of the balloon catheter system (20). In this embodiment, the catheter further includes a proximal balloon (50) and a distal balloon (52) positioned along the catheter (22) on both sides of the double balloon assembly (32, 34). The catheter includes two additional lumens, one in fluid communication with the proximal balloon (50) and the other in fluid communication with the distal balloon (52). It should be noted that a single lumen can be provided instead of the two lumens to supply fluid to both proximal and distal balloons.

In an advantageous embodiment, the proximal and distal balloons (50, 52) are provided with a textured surface that assists in gripping of the balloons to the surrounding tissue upon inflation to facilitate secure positioning of the balloons in the nasal cavity or passage. The walls of the proximal and distal balloons (50, 52) can be made transparent to enable visualization via an imaging device disposed inside the balloons, as described above with respect to the inner and outer balloons.

Once the balloon catheter is introduced into a sinus opening and positioned at a target site, the proximal balloon (50) and the distal balloon (52) are inflated by supplying fluid thereto by the pump (24) via the lumens, as discussed above. The proximal and distal balloons (50, 52) are inflated simultaneously to create a chamber therebetween (54), into which the therapeutic and/or diagnostic agents are delivered through the openings in the outer balloon (32). Alternatively, the distal balloon (52) is inflated first and is used as an anchor to secure the balloon catheter assembly at the target site, and then the proximal balloon (50) is inflated to create the chamber (54).

The chamber (54) functions to isolate the target treatment site from the surrounding tissue, which is desirable to ensure more efficient saturation of the treatment site with the agent being delivered and to prevent leakage of the agents to other nasal cavities and passages. Additionally, by creating the fluidly isolated chamber (54), it is possible to change volumetric pressure within the chamber to facilitate extravasation of the agent into target tissue. This can be achieved by repeatedly inflating and deflating the inner balloon (32) and/or the outer balloon (34) such that the fluid pressure in the chamber (54) is increased and decreased.

Once the agents have been delivered and extravasted into the tissue at the target site, any remaining agent can be evacuated from the chamber (54) via the same openings and lumens through which they were supplied to the chamber (54) using suction. In certain advantageous embodiments, the fluid source (24) produces a negative pressure to vacuum out the agents. Alternatively, additional lumens and corresponding openings may be employed in the manner previously described to evacuate the agents through lumens different from those used to supply the agents to the chamber (54). Regardless, the various lumens and corresponding openings can be used to cyclically deliver and evacuate the agents and various other fluids instantly, sequentially, intermittently and/or continuously over designated time intervals.

Additionally, as described above, one of the lumens of the catheter (22) may be used to supply an irrigation fluid. For example, once the desired therapeutic and/or diagnostic agent has been delivered to the target treatment site and has sufficiently saturated the treatment site, the remaining agent can be vacuumed out of the chamber (54). The chamber (54) can then be irrigated, lavaged, and suctioned to remove any residual agent and/or other matter, such as mucus.

Figure 8A:
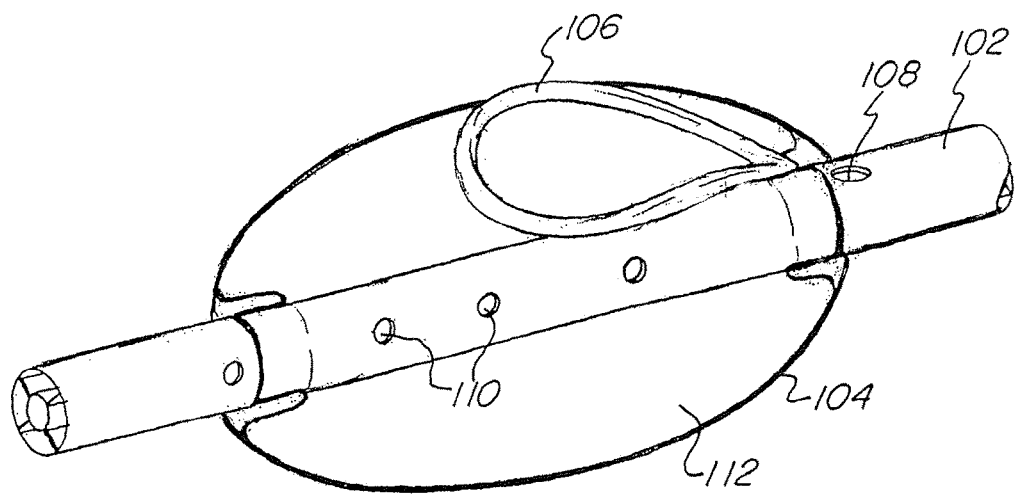
FIGS. 8A-8D illustrate the balloon catheter assembly of FIG. 1, with protrusions positioned between the inner balloon and the outer balloon.

FIGS. 8A-8D illustrate another advantageous embodiment of the inner balloon and the outer balloon of the balloon catheter system. FIG. 8A illustrates a portion of a catheter (102) with an inner balloon (104) disposed thereon. A wall of the inner balloon (104) has an inner surface and an outer surface, and at least partially encloses an inflation chamber (112). The catheter (102) includes a plurality of openings (110), through which fluid is supplied from a fluid source to the inflation chamber (112) via one of the catheter lumens to inflate the inner balloon (104). The catheter also includes at least one opening (108) positioned outside of the inner balloon (104), through which a therapeutic and/or diagnostic agent is supplied via another lumen of the catheter (102). The outer surface of the inner balloon's wall has a protrusion (106) extending above the wall surface. The protrusion (106) has a tear-drop shape terminating at the distal end of the inner balloon (104) adjacent to the opening (108).

Figure 8B:
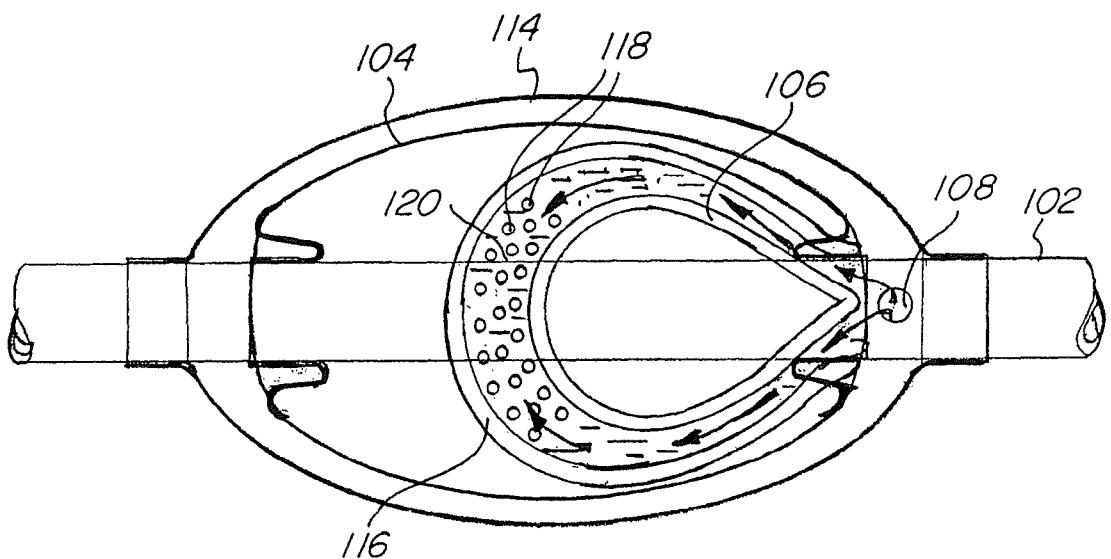

FIG. 8B illustrates a top view of the catheter assembly (102), showing both the inner balloon (104) and an outer balloon (114). A wall of the outer balloon (114) has a protrusion (116) on an inner surface, extending beyond the inner surface of the outer balloon (116) towards the outer surface of the inner balloon (104). The protrusion (116) is shaped such that it corresponds to the shape of the protrusion (106), forming a channel (120) defined by the two protrusions (106, 116) between the inner surface of the outer balloon (114) and the outer surface of the inner balloon (104). The wall of the outer balloon (114) has a plurality of openings (118) positioned adjacent to the channel (120). When the therapeutic and/or diagnostic agent is supplied to the space between the two balloons (104, 114) through the opening (108) in the catheter (102), the agent flows through the channel (120) and is then urged out of the openings (118) into adjacent tissue.

Figure 8C:
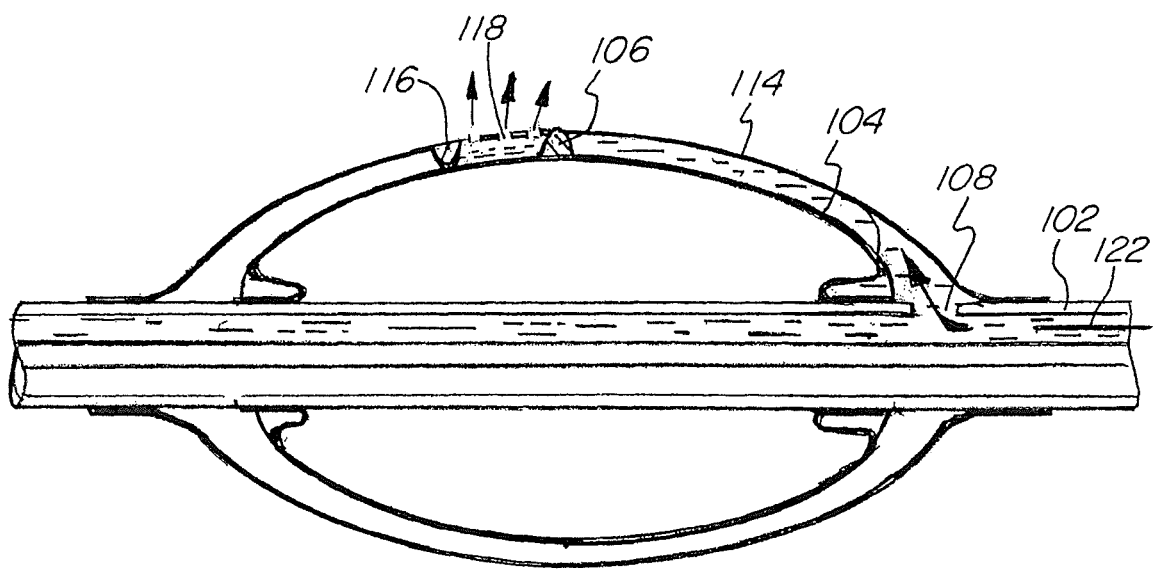
Figure 8D:
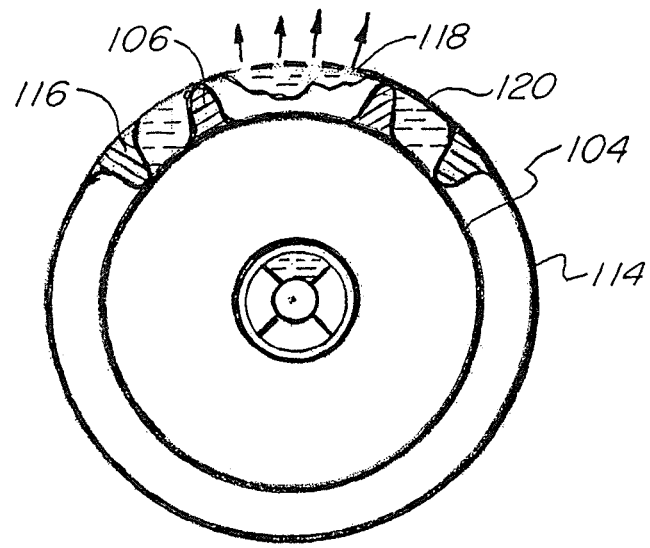

This is further illustrated in FIGS. 8C and 8D, which show longitudinal and transverse cross-sectional views of the catheter assembly (102). The therapeutic and/or diagnostic agent is delivered via a catheter lumen (122) through the opening (108) and into the space between the inner balloon (104) and the outer balloon (114). The agent collects in the channel formed by the protrusion (106) on the outer surface of the inner balloon (104) and the protrusion (116) on the inner surface of the outer balloon (114). As the inner balloon (104) is inflated, the agent is pushed out of the openings (118) into the tissue. Such design allows for more precise delivery of the agent to the targeted tissue by preventing or minimizing the agent from exiting the targeted tissue area.

The protrusions (106, 116) on the inner balloon (104) and the outer balloon (114) are formed during the balloon manufacturing process. For example, a mandrel used during the balloon molding process can have depressions that correspond to the desired protrusions to be formed on the surface of the balloons. When the mandrel is dipped into the balloon material, such as latex or yulex, the material fills the depressions. The formed balloon is then removed from the mandrel and turned inside out such that the excess material in the depressions is now on the outside surface of the balloon, forming the protrusions.

Figure 9A:
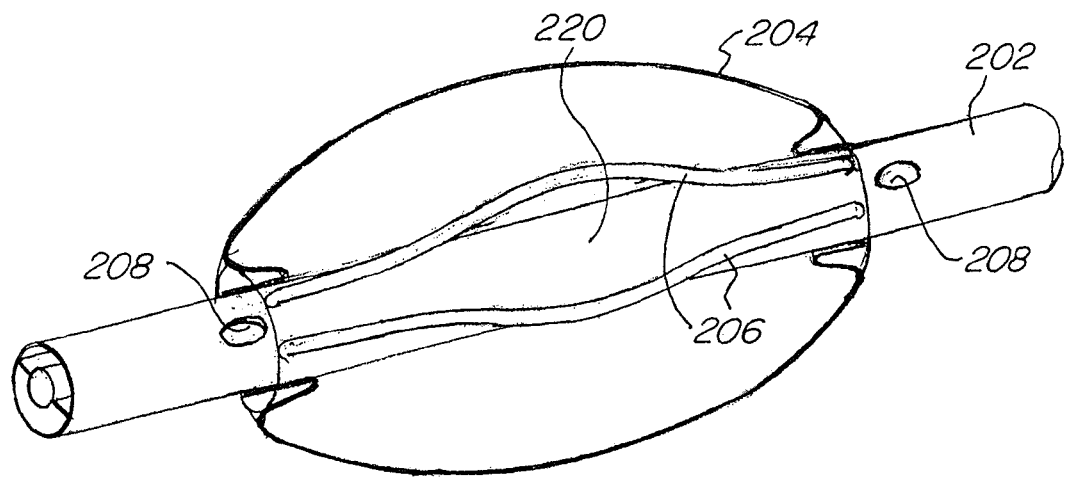
FIGS. 9A-9D illustrate the balloon catheter assembly of FIG. 1, with protrusions positioned between the inner and outer balloons and on the outer wall of the outer balloon.

FIGS. 9A-9D illustrate an additional embodiment of the double balloon construct of the present invention. In this embodiment, as shown in FIG. 9A, an inner balloon (204) has length-wise protrusions (206) on the outer surface of the balloon that run from a distal end to a proximal end of the balloon. The protrusions (206) form a channel (220) therebetween that originates and terminates at openings (208) in the catheter (202) through which the agent is supplied. The middle section of the channel (220) is wider to allow the agent to pool in that section.

Figure 9B:
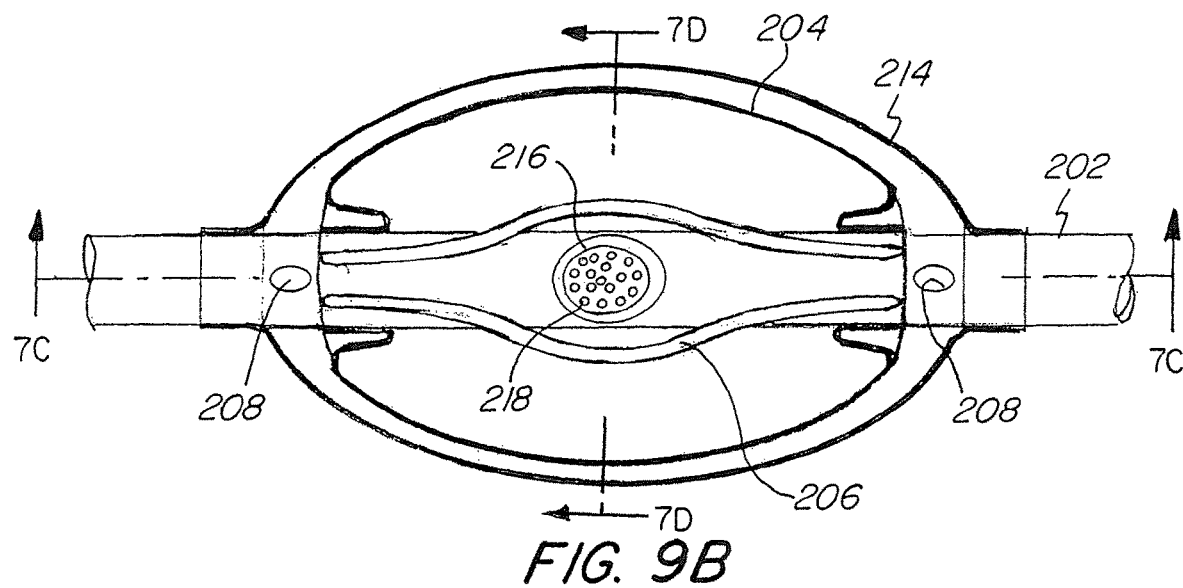
Figure 9C:
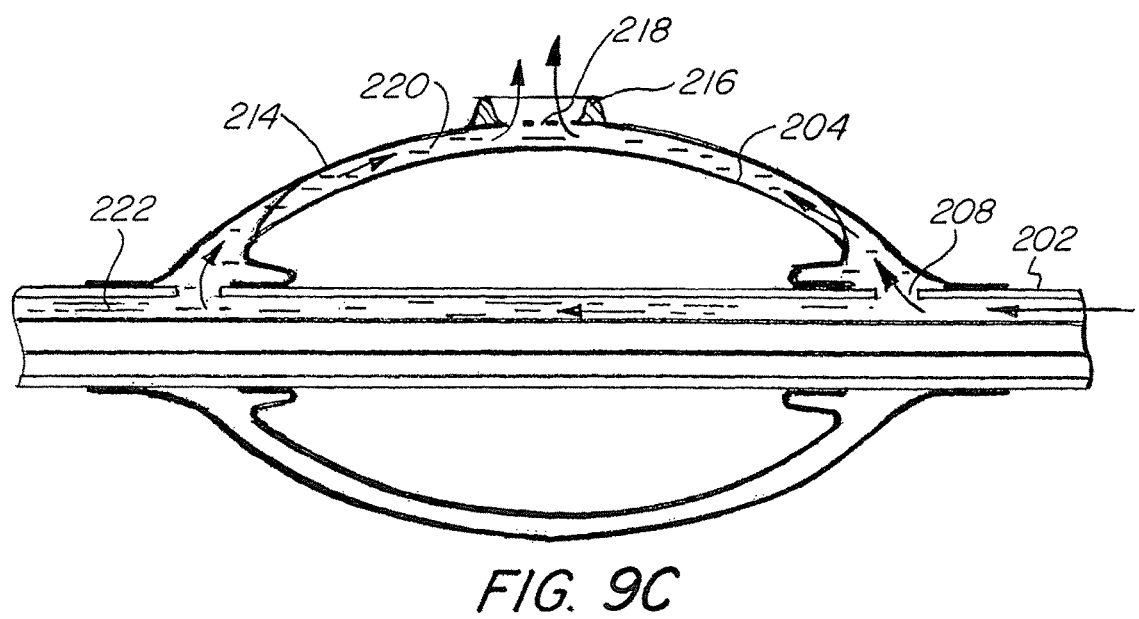
Figure 9D:
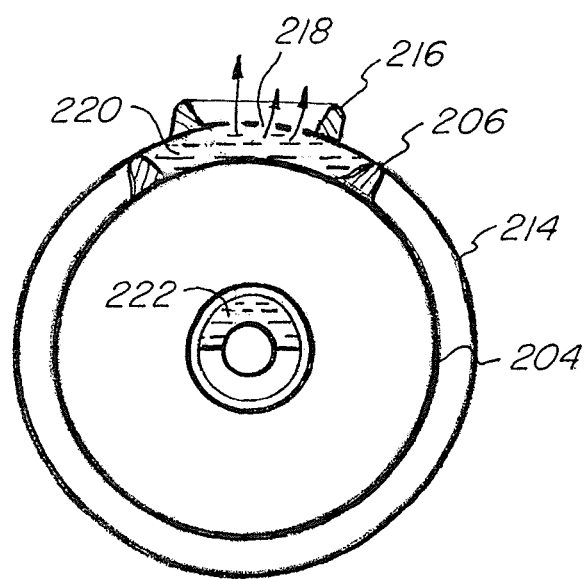

An outer balloon (214) has a circular protrusion (216) provided on the outer surface of the balloon (214) and extending outwardly from the balloon (214), as illustrated in FIG. 9B. A wall of the outer balloon (214) has perforations (218) in the area inside the circular protrusion (216). As shown in FIGS. 9C and 9D, the therapeutic and/or diagnostic agent is delivered via a catheter lumen (222) through the openings (208) into the space between the inner balloon (204) and the outer balloon (214). The agent is directed through the channel (220) and collects in the wider section of the channel. The inner balloon (204) is inflated such that the circular protrusion (216) of the outer balloon (214) is pressed against the target tissue area and the agent is pushed out of the openings (218) into the target tissue. The circular protrusion (216) assists in containing the agent within an isolated area such that it is delivered directly to the target tissue area.

It should be understood that the embodiments depicted in FIGS. 8A-8D and 9A-9D are only illustrative and that other configurations of the balloons can be used without departing from the spirit of the invention. For example, the protrusions can be provided only on the surface of the inner balloon or only the surface of the outer balloon. Further, the protrusions can have any desirable shape and configuration depending on where the therapeutic and/or diagnostic agent needs to be delivered.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of localized delivery of a therapeutic and/or diagnostic agent to nasal tissue or cavities, comprising the steps of:
    inserting a catheter into a nasal cavity, said catheter comprising
        an outer balloon having a wall with at least one opening therethrough and an inner surface; and
        an inner balloon at least partially disposed in said outer balloon, said inner balloon at least partially enclosing an inflation chamber and having an outer surface defining a space between the outer surface of said inner balloon and the inner surface of said outer balloon;
    supplying the therapeutic and/or diagnostic agent to the space between the outer surface of said inner balloon and the inner surface of said outer balloon via a first lumen of said catheter; and
    inflating said inner balloon by supplying fluid to the inflation chamber via a second lumen of said catheter to urge the therapeutic and/or diagnostic agent out of the at least one opening in the wall of said outer balloon and into nasal tissue.

2. The method of claim 1, further comprising a step of directing the therapeutic and/or diagnostic agent to a localized area in the nasal cavity via at least one protrusion formed by at least one of an inner balloon wall and the wall of the outer balloon.

3. The method of claim 2, wherein the step of directing the therapeutic and/or diagnostic agent to the localized area in the nasal cavity comprises supplying the therapeutic and/or diagnostic agent to a channel defined by a first protrusion formed by the inner surface of said outer balloon and a second protrusion formed by the outer surface of said inner balloon.

4. The method of claim 1, wherein the therapeutic and/or diagnostic agent comprises an anesthetic.

5. The method of claim 1, wherein the therapeutic and/or diagnostic agent comprises a mucolytic agent.

6. The method of claim 1, wherein the therapeutic and/or diagnostic agent comprises an antihistamine agent.

7. The method of claim 1, further comprising a step of heating at least one of the inner balloon and the outer balloon.

8. The method of claim 1, further comprising a step of dilating a nasal passage by placing the inner and outer balloons in the passage and inflating the inner balloon such that the outer balloon contacts walls of the nasal cavity and dilates the cavity.

9. The method of claim 1, further comprising a step of mitigating bleeding in the nasal cavity by applying pressure to a cavity wall via the outer balloon.

10. The method of claim 1, further comprising a step of visualizing the nasal cavity via an imaging device disposed in said catheter.

11. The method of claim 1, further comprising a step of delivering an irrigation fluid to the nasal cavity and suctioning the irrigation fluid out of the nasal cavity with the catheter.

12. The method of claim 1, wherein said catheter comprises a flexible steering member disposed at a distal end of the catheter and the method further comprises a step of maneuvering the catheter through nasal anatomy via said steering member.

13. The method of claim 1, wherein the wall of said outer balloon has an abrasive outer surface, and wherein the step of inflating said inner balloon comprises contacting the nasal tissue with the abrasive surface such that it abrades the tissue.

14. The method of claim 1, wherein the step of delivering the therapeutic and/or diagnostic agent to tissue further comprises inflating said inner balloon until the wall of said outer balloon contacts the nasal tissue.

15. The method of claim 1, wherein the step of inflating said inner balloon comprises supplying fluid thereto with a fluid source.

16. The method of claim 15, further comprising a step of monitoring at least one patient vital sign via a monitoring device and controlling a pressure to which the inner balloon is inflated via said fluid source based at least in part on the at least one monitored patient vital sign.

17. The method of claim 15, further comprising a step of monitoring at least one patient vital sign via a monitoring device and controlling a supply of the therapeutic and/or diagnostic agent via said fluid source based at least in part on the at least one monitored patient vital sign.

18. The method of claim 15, further comprising a step of repeatedly deflating and inflating said inner balloon in pulsed fashion by supplying fluid thereto via said fluid source.

19. The method of claim 1, further comprising a step of measuring at least one characteristic of tissue in the nasal cavity via at least one sensor.

20. The method of claim 1, wherein said catheter further comprises a distal balloon positioned distally of said inner and outer balloons and a proximal balloon positioned proximally of said inner and outer balloons, wherein the method further comprises a step of inflating the distal and proximal balloons by supplying fluid thereto via at least one additional lumen of said catheter to create a chamber between the distal and proximal balloons, and wherein the step of urging the therapeutic and/or diagnostic agent into the nasal tissue comprises delivering the therapeutic and/or diagnostic agent to said chamber.

21. The method of claim 1, wherein the wall of said outer balloon has an outer surface comprising a mesh sleeve of elastic yarn.

22. The method of claim 21, wherein the mesh sleeve is radiopaque.

23. The method of claim 1, wherein the at least one therapeutic and/or diagnostic agent further comprises at least one biomarker.

* * * * *